US012806324B2

(12) United States Patent
Riccardi et al.

(10) Patent No.: US 12,806,324 B2
(45) Date of Patent: Nov. 24, 2026

(54) METHOD OF REGULATING GENE EXPRESSION

(71) Applicant: EnClear Therapies, Inc., Newburyport, MA (US)

(72) Inventors: Gianna N. Riccardi, South Berwick, ME (US); William X. Siopes, Jr., Lowell, MA (US); Marcie Glicksman, Salem, MA (US); Anthony DePasqua, Newburyport, MA (US); Kevin Kalish, Newburyport, MA (US); Joshua G. Vose, Seattle, WA (US); Rajan Patel, Newburyport, MA (US)

(73) Assignee: EnClear Therapies, Inc., Newburyport, MA (US)

( * ) Notice: Subject to any disclaimer, the term of this patent is extended or adjusted under 35 U.S.C. 154(b) by 769 days.

(21) Appl. No.: 17/848,211

(22) Filed: Jun. 23, 2022

(65) Prior Publication Data

US 2022/0313890 A1 Oct. 6, 2022

Related U.S. Application Data

(63) Continuation-in-part of application No. 17/669,883, filed on Feb. 11, 2022, now Pat. No. 12,350,416,
(Continued)

(51) Int. Cl.

*A61M 1/36* (2006.01)
*A61M 1/16* (2006.01)
*A61M 27/00* (2006.01)

(52) U.S. Cl.

CPC ............ *A61M 1/3687* (2013.01); *A61M 1/16* (2013.01); *A61M 1/1601* (2014.02);
(Continued)

(58) Field of Classification Search

CPC ........ A61M 27/006; A61M 2027/0004; A61M 2202/0464; A61M 1/14; A61M 1/34; A61M 1/36; A61M 1/3687
See application file for complete search history.

(56) References Cited

U.S. PATENT DOCUMENTS 3,929,992 A 12/1975 Sehgal et al.
4,316,885 A 2/1982 Rakhit
(Continued)

FOREIGN PATENT DOCUMENTS

CN 203604173 U 5/2014
CN 106362226 A 2/2017
(Continued)

OTHER PUBLICATIONS

Mcrae et al., Mapping the active sites of bovine thrombin, factor IXa, factor Xa, factor XIa, factor XIIa, plasma kallikrein, and trypsin with amino acid and peptide thioesters: development of new sensitive substrates. Biochemistry 1981, 20, 25, pp. 7196-7206.
(Continued)

*Primary Examiner* — Leslie R Deak
(74) *Attorney, Agent, or Firm* — Nutter McClennen & Fish LLP

(57) ABSTRACT

A method to regulate patient gene expression by controllably circulating antisense oligonucleotide material (ASO) through a closed fluid circuit formed between the patient's ventricle and lumbar regions. To that end, after coupling a fluid channel between those regions, such embodiments add ASO to the fluid channel (preferably after the channel is primed with CSF) and energize a pump to controllably flow the CSF and the ASO mixed with the CSF. CSF/ASO fluid flow may be managed to localize treatment (e.g., providing
(Continued)

*Method to manually program method of delivery* deep brain distribution) while minimizing toxicity potentially caused by the ASO to certain nerves (e.g., the peripheral nerve).

16 Claims, 14 Drawing Sheets

Related U.S. Application Data which is a continuation of application No. 17/062,440, filed on Oct. 2, 2020, now Pat. No. 11,278,657, which is a continuation of application No. PCT/US2020/027683, filed on Apr. 10, 2020, application No. 17/848,211 is a continuation-in-part of application No. 17/495,682, filed on Oct. 6, 2021, application No. 17/848,211 is a continuation-in-part of application No. 17/489,620, filed on Sep. 29, 2021, now Pat. No. 12,337,140.

(60) Provisional application No. 62/832,486, filed on Apr. 11, 2019, provisional application No. 62/960,861, filed on Jan. 14, 2020, provisional application No. 63/088,401, filed on Oct. 6, 2020, provisional application No. 63/084,996, filed on Sep. 29, 2020, provisional application No. 63/117,975, filed on Nov. 24, 2020, provisional application No. 63/214,239, filed on Jun. 23, 2021.

(52) U.S. Cl.
CPC ......... *A61M 27/006* (2013.01); *A61M 1/3655* (2013.01); *A61M 1/3659* (2014.02); *A61M 2027/004* (2013.01); *A61M 2202/0464* (2013.01); *A61M 2205/103* (2013.01); *A61M 2205/12* (2013.01); *A61M 2205/3334* (2013.01); *A61M 2205/3344* (2013.01); *A61M 2205/3379* (2013.01); *A61M 2210/1003* (2013.01); *A61M 2210/1039* (2013.01)

(56) References Cited

U.S. PATENT DOCUMENTS

| | | | |
|---|---|---|---|
| 4,366,241 | A | 12/1982 | Tom et al. |
| 4,376,110 | A | 3/1983 | David et al. |
| 4,382,445 | A | 5/1983 | Sommers |
| 4,517,288 | A | 5/1985 | Giegel et al. |
| 4,650,803 | A | 3/1987 | Stella et al. |
| 4,655,745 | A | 4/1987 | Corbett |
| 4,830,849 | A | 5/1989 | Osterholm |
| 4,837,168 | A | 6/1989 | de Jaeger et al. |
| 4,950,232 | A | 8/1990 | Ruzicka et al. |
| 5,023,263 | A | 6/1991 | Von Burg |
| 5,023,264 | A | 6/1991 | Caufield et al. |
| 5,100,883 | A | 3/1992 | Schiehser |
| 5,118,677 | A | 6/1992 | Caufield |
| 5,118,678 | A | 6/1992 | Kao et al. |
| 5,120,842 | A | 6/1992 | Failli et al. |
| 5,130,307 | A | 7/1992 | Failli et al. |
| 5,162,333 | A | 11/1992 | Failli et al. |
| 5,177,203 | A | 1/1993 | Failli et al. |
| 5,221,670 | A | 6/1993 | Caufield |
| 5,233,036 | A | 8/1993 | Hughes |
| 5,256,790 | A | 10/1993 | Nelson |
| 5,258,389 | A | 11/1993 | Goulet et al. |
| 5,260,300 | A | 11/1993 | Hu |
| 5,262,423 | A | 11/1993 | Kao |
| 5,302,584 | A | 4/1994 | Kao et al. |
| 5,362,718 | A | 11/1994 | Skotnicki et al. |
| 5,373,014 | A | 12/1994 | Failli et al. |
| 5,378,836 | A | 1/1995 | Kao et al. |
| 5,385,908 | A | 1/1995 | Nelson et al. |
| 5,385,909 | A | 1/1995 | Nelson et al. |
| 5,385,910 | A | 1/1995 | Ocain et al. |
| 5,389,639 | A | 2/1995 | Failli et al. |
| 5,391,730 | A | 2/1995 | Skotnicki et al. |
| 5,405,316 | A | 4/1995 | Magram |
| 5,411,967 | A | 5/1995 | Kao et al. |
| 5,434,260 | A | 7/1995 | Skotnicki et al. |
| 5,463,048 | A | 10/1995 | Skotnicki et al. |
| 5,470,318 | A | 11/1995 | Griffith et al. |
| 5,480,988 | A | 1/1996 | Failli et al. |
| 5,480,989 | A | 1/1996 | Kao et al. |
| 5,489,680 | A | 2/1996 | Failli et al. |
| 5,491,231 | A | 2/1996 | Nelson et al. |
| 5,504,091 | A | 4/1996 | Molnar-Kimber et al. |
| 5,531,673 | A | 7/1996 | Helenowski |
| 5,563,145 | A | 10/1996 | Failli et al. |
| 5,665,772 | A | 9/1997 | Cottens et al. |
| 5,780,462 | A | 7/1998 | Lee et al. |
| 5,957,912 | A | 9/1999 | Heitzmann |
| 6,193,691 | B1 | 2/2001 | Beardsley |
| 6,210,346 | B1 | 4/2001 | Hall et al. |
| 6,273,913 | B1 | 8/2001 | Wright et al. |
| 6,277,983 | B1 | 8/2001 | Shaw et al. |
| 6,358,969 | B1 | 3/2002 | Shelley et al. |
| 6,471,960 | B1 | 10/2002 | Anderson |
| 6,585,764 | B2 | 7/2003 | Wright et al. |
| 6,599,275 | B1 | 7/2003 | Fischer, Jr. |
| 6,670,168 | B1 | 12/2003 | Katz et al. |
| 6,689,085 | B1 | 2/2004 | Rubenstein et al. |
| 6,696,488 | B2 | 2/2004 | Wolfe et al. |
| 6,808,536 | B2 | 10/2004 | Wright et al. |
| 6,916,310 | B2 | 7/2005 | Sommerich |
| 7,025,739 | B2 | 4/2006 | Saul |
| 7,037,288 | B2 | 5/2006 | Rosenberg et al. |
| 7,331,940 | B2 | 2/2008 | Sommerich |
| 7,662,140 | B2 | 2/2010 | Heruth et al. |
| 7,717,871 | B2 | 5/2010 | Odland |
| 7,763,142 | B2 | 7/2010 | Watson |
| 7,887,503 | B2 | 2/2011 | Geiger |
| 8,088,091 | B2 | 1/2012 | Thomas et al. |
| 8,137,334 | B2 | 3/2012 | Heruth et al. |
| 8,206,334 | B2 | 6/2012 | Kralick et al. |
| 8,216,173 | B2 | 7/2012 | Dacey, Jr. et al. |
| 8,292,856 | B2 | 10/2012 | Bertrand et al. |
| 8,435,204 | B2 | 5/2013 | Lad et al. |
| 9,097,723 | B2 | 8/2015 | Fathollahi et al. |
| 9,138,537 | B2 | 9/2015 | Miesel |
| 9,220,424 | B2 | 12/2015 | Wilson et al. |
| 9,421,348 | B2 | 8/2016 | Lenihan et al. |
| 9,603,792 | B2 | 3/2017 | John |
| 9,629,987 | B2 | 4/2017 | Anand et al. |
| 9,682,193 | B2 | 6/2017 | Anand et al. |
| 9,687,670 | B2 | 6/2017 | Dacey, Jr. et al. |
| 9,744,338 | B2 | 8/2017 | East et al. |
| 9,770,180 | B2 | 9/2017 | Radojicic |
| 9,895,518 | B2 | 2/2018 | Lad et al. |
| 9,919,138 | B2 | 3/2018 | Lenihan et al. |
| 10,258,781 | B2 | 4/2019 | Choi et al. |
| 10,272,188 | B1 | 4/2019 | Geiger et al. |
| 10,441,770 | B2 | 10/2019 | Singh et al. |
| 10,549,035 | B2 | 2/2020 | Hayek |
| 10,653,713 | B2 | 5/2020 | Thakker et al. |
| 10,695,484 | B1 | 6/2020 | Radojicic |
| 10,864,323 | B2 | 12/2020 | Gerrans |
| 11,278,657 | B2 | 3/2022 | DePasqua et al. |
| 11,534,592 | B2 | 12/2022 | Singh et al. |
| 2002/0004580 | A1 | 1/2002 | Fueyo et al. |
| 2002/0025521 | A1 | 2/2002 | Lu et al. |
| 2003/0060436 | A1 | 3/2003 | Schneider |
| 2003/0135148 | A1 | 7/2003 | Dextradeur et al. |
| 2004/0068241 | A1 | 4/2004 | Fischer |
| 2004/0110250 | A1 | 6/2004 | Wischik et al. |
| 2004/0138153 | A1 | 7/2004 | Ramesh et al. |
| 2004/0185042 | A1 | 9/2004 | Scheiflinger et al. |
| 2004/0220510 | A1 | 11/2004 | Koullick et al. |
| 2004/0236309 | A1 | 11/2004 | Yang |
| 2006/0025726 | A1 | 2/2006 | Fischer et al. |
| 2006/0074388 | A1 | 4/2006 | Dextradeur et al. |
| 2006/0079740 | A1 | 4/2006 | Silver et al. |

(56) References Cited

U.S. PATENT DOCUMENTS

| | | | |
|---|---|---|---|
| 2006/0264897 | A1 | 11/2006 | Lobl et al. |
| 2007/0167867 | A1 | 7/2007 | Wolf |
| 2007/0173787 | A1 | 7/2007 | Huang et al. |
| 2007/0243179 | A1 | 10/2007 | Elia |
| 2008/0082036 | A1 | 4/2008 | Trescony et al. |
| 2008/0242590 | A1 | 10/2008 | Andersson et al. |
| 2009/0131857 | A1 | 5/2009 | Geiger |
| 2010/0022896 | A1 | 1/2010 | Yadav et al. |
| 2010/0030196 | A1 | 2/2010 | Hildebrand et al. |
| 2010/0234792 | A1 | 9/2010 | Dacey, Jr. et al. |
| 2011/0033463 | A1 | 2/2011 | Thakker et al. |
| 2012/0238835 | A1 | 9/2012 | Hyde et al. |
| 2012/0238936 | A1 | 9/2012 | Hyde et al. |
| 2013/0197422 | A1 | 8/2013 | Browd et al. |
| 2013/0273203 | A1 | 10/2013 | Oestergaard et al. |
| 2014/0018257 | A1 | 1/2014 | Suga et al. |
| 2014/0206102 | A1 | 7/2014 | Petrucelli et al. |
| 2014/0303455 | A1 | 10/2014 | Shachar et al. |
| 2014/0377319 | A1 | 12/2014 | Leuthardt et al. |
| 2015/0005800 | A1 | 1/2015 | Anile |
| 2015/0094644 | A1 | 4/2015 | Lenihan et al. |
| 2015/0201882 | A1 | 7/2015 | Swoboda et al. |
| 2015/0374898 | A1 | 12/2015 | Fujieda et al. |
| 2016/0002627 | A1 | 1/2016 | Bennett et al. |
| 2016/0025747 | A1 | 1/2016 | Ranum et al. |
| 2016/0089521 | A1 | 3/2016 | Dragoon et al. |
| 2016/0183819 | A1 | 6/2016 | Burnett et al. |
| 2016/0331897 | A1 | 11/2016 | Anand et al. |
| 2016/0361365 | A1 | 12/2016 | Lee et al. |
| 2017/0059586 | A1 | 3/2017 | Petrucelli et al. |
| 2017/0095649 | A1 | 4/2017 | Vase et al. |
| 2017/0137492 | A1 | 5/2017 | Looby |
| 2017/0157038 | A1 | 6/2017 | Peyman |
| 2017/0157374 | A1 | 6/2017 | Hedstrom et al. |
| 2017/0203084 | A1 | 7/2017 | Lad et al. |
| 2017/0313687 | A1 | 11/2017 | Hendrickson et al. |
| 2018/0028746 | A1 | 2/2018 | Abrams et al. |
| 2018/0185058 | A1 | 7/2018 | Anand et al. |
| 2018/0371010 | A1 | 12/2018 | Vassylyev et al. |
| 2019/0009014 | A1 | 1/2019 | Chen et al. |
| 2019/0048371 | A1 | 2/2019 | Basheer et al. |
| 2019/0083303 | A1 | 3/2019 | Khanna |
| 2019/0085336 | A1 | 3/2019 | Zhu et al. |
| 2019/0089521 | A1 | 3/2019 | Coulthard et al. |
| 2019/0317099 | A1 | 10/2019 | Halbert et al. |
| 2020/0001059 | A1 | 1/2020 | Campbell et al. |
| 2020/0046952 | A1 | 2/2020 | Vase |
| 2020/0046954 | A1 | 2/2020 | Lad et al. |
| 2020/0324006 | A1 | 10/2020 | Paul et al. |
| 2020/0330497 | A1 | 10/2020 | Marcotulli et al. |
| 2021/0023293 | A1 | 1/2021 | DePasqua et al. |
| 2021/0033620 | A1 | 2/2021 | Porter et al. |
| 2021/0077016 | A1 | 3/2021 | Bodner |
| 2021/0145944 | A1 | 5/2021 | Navia et al. |
| 2021/0154276 | A1 | 5/2021 | Navia et al. |
| 2021/0162173 | A1 | 6/2021 | Singh et al. |
| 2022/0096743 | A1 | 3/2022 | Riccardi et al. |
| 2022/0096744 | A1 | 3/2022 | Riccardi et al. |
| 2022/0096745 | A1 | 3/2022 | Riccardi et al. |
| 2022/0105322 | A1 | 4/2022 | Riccardi et al. |
| 2022/0134076 | A1 | 5/2022 | Bodner |
| 2022/0160947 | A1 | 5/2022 | DePasqua et al. |
| 2022/0257854 | A1 | 8/2022 | Bodner et al. |
| 2022/0355015 | A1 | 11/2022 | Patel et al. |
| 2022/0370716 | A1 | 11/2022 | Martin et al. |
| 2022/0379010 | A1 | 12/2022 | Martin et al. |
| 2022/0401645 | A1 | 12/2022 | Morse et al. |
| 2023/0001165 | A1 | 1/2023 | Bourouiba et al. |
| 2023/0056486 | A1 | 2/2023 | Navia et al. |

FOREIGN PATENT DOCUMENTS

| | | | |
|---|---|---|---|
| EP | 1481697 | A1 | 12/2004 |
| EP | 1731182 | A1 | 12/2006 |
| EP | 3294398 | A1 | 3/2018 |
| EP | 3833251 | A1 | 6/2021 |
| EP | 4030988 | A1 | 7/2022 |
| JP | 2002/136295 | A | 5/2002 |
| WO | 98/02441 | A2 | 1/1998 |
| WO | 99/13886 | A1 | 3/1999 |
| WO | 99/15530 | A1 | 4/1999 |
| WO | 2000/056335 | A1 | 9/2000 |
| WO | 01/14387 | A1 | 3/2001 |
| WO | 2001/039819 | A2 | 6/2001 |
| WO | 2003015710 | A2 | 2/2003 |
| WO | 03/057218 | A1 | 7/2003 |
| WO | 2003/015710 | A3 | 2/2004 |
| WO | 2004/058337 | A1 | 7/2004 |
| WO | 2004/091444 | A2 | 10/2004 |
| WO | 2008/105959 | A2 | 9/2008 |
| WO | 2008140546 | A2 | 11/2008 |
| WO | 2010123558 | A1 | 10/2010 |
| WO | 2011114260 | A1 | 9/2011 |
| WO | 2014/159247 | A1 | 10/2014 |
| WO | 2014/159757 | A2 | 10/2014 |
| WO | 2015/049588 | A2 | 4/2015 |
| WO | 2014/124365 | A3 | 10/2015 |
| WO | 2016/143227 | A1 | 9/2016 |
| WO | 2016183123 | A1 | 11/2016 |
| WO | 2017096228 | A1 | 6/2017 |
| WO | 2018005621 | A1 | 1/2018 |
| WO | 2018/160993 | A1 | 9/2018 |
| WO | 2019028006 | A1 | 2/2019 |
| WO | 2019/100074 | A1 | 5/2019 |
| WO | 2020/023417 | A1 | 1/2020 |
| WO | 2020/023418 | A1 | 1/2020 |
| WO | 2020/033773 | A1 | 2/2020 |
| WO | 2020064875 | A1 | 4/2020 |
| WO | 2020/0149993 | A1 | 7/2020 |
| WO | 2020/210634 | A1 | 10/2020 |
| WO | 2021/055100 | A1 | 3/2021 |
| WO | 2022072558 | A1 | 4/2022 |
| WO | 2022/173620 | A1 | 8/2022 |
| WO | 2022/246042 | A1 | 11/2022 |

OTHER PUBLICATIONS

Menendez-Gonzalez, M., et al., "Targeting Beta-Amyloid at the CSF: A New Therapeutic Strategy in Alzheimer's Disease," Frontiers in Aging Neuroscience, vol. 10, 2018, pp. 1-8.

Narasimhan, S., et al., "Pathological Tau Strains from Human Brains Recapitulate the Diversity of Tauopathies in Nontransgenic Mouse Brain," The Jorunal of Neuroscience, vol. 37, Issue 47, 2017, pp. 11406-11423.

Neumann, M., et al., "Ubiquitinated TDP-43 in frontotemporal lobar degeneration and amyotrophic lateral sclerosis," Science, vol. 314, 2006, pp. 130-133.

Ohki, Y., et al., "Glycine-alanine dipeptide repeat protein contributes to toxicity in a zebrafish model of C9orf72 associated neurodegeneration," Molecular Neurodegeneration (2017) 12:6, pp. 1-11.

Ozcelik, A., et al., "Acoustic tweezers for the life sciences," Nature Methods vol. 15, 2018, pp. 1021-1028.

Paraskevas, G., et al., "The emerging TDP-43 proteinpathy" Neuroimmunol Neuroinflammation 5:17 (Year 2018).

Pardridge, W., et al., "CSF, blood-brain barrier, and brain drug delivery," Expert Opinion on Drug Delivery, vol. 13, 2016, pp. 1-13.

Patel, A., et al., "Identification and enumeration of circulating tumor cells in the cerebrospinal fluid of breast cancer patents with central nervous system metastases," Oncotarget, vol. 2, No. 10, 2011, pp. 752-760.

Paulson, H., et al., "Genetics of Dementia," Seminars in Neurology, vol. 31, pp. 449-360.

Phukan, J., et al., "Cognitive impairment in amyotrophic lateral sclerosis," The Lancet Neurology, vol. 6, Issue 11, pp. 994-1003.

Poreba, M., et al., "Current Strategies for Probing Substrate Specificity of Proteases," Current Medicinal Chemistry, vol. 17, Issue 33, 2010, pp. 3968-3995.

Quinn, J., et al., "Tau Proteolysis in the Pathogenesis of Tauopathies: Neurotoxic Fragments and Novel Biomarkers," Journal of Alzheimer's Disease, vol. 63, No. 1, 2018, pp. 13-33.

(56) References Cited

OTHER PUBLICATIONS

Reinhard, M., et al., "Blood-Brain Barrier Disruption By Low-Frequency Ultrasound," Stroke, vol. 37, 2006, pp. 1546-1548.
Renton, A., et al., "A Hexanucleotide Repeat Expansion in C9ORF72 Is the Cause of Chromosome 9p21-Linked ALS-FTD," Neuron, vol. 27, Issue 2, pp. 257-268.
Sonabend, A., et al., "Overcoming the Blood-Brain Barrier with an Implantable Ultrasound Device," Clinical Cancer Research, vol. 25, Issue 13, 2019, pp. 3750-3752.
Song, J., et al., "Investigation of standing wave formation in a human skull for a clinical prototype of a large-aperture, transcranial MR-guided Focused Ultrasound (MRgFUS) phased array: An experimental and simulation study," IEEE Transactions on Biomedical Engineering, vol. 59, Issue 2, 2012, pp. 435-444.
Steele, J., et al., "Progressive Supranuclear Palsy A Heterogeneous Degeneration Involving the Brain Stem, Basal Ganglia and Cerebellum With Vertical Gaze and Pseudobulbar Palsy, Nuchal Dystonia and Dementia," Arch Neurol. vol. 10, No. 4, 1964, pp. 333-359.
Takalo, M., et al., "Protein aggregation and degradation mechanisms in neurodegenerative diseases," American Journal of Neurodegenerative Disease, 2013; 2(1), pp. 1-14.
Tarasoff-Conway, J., et al., "Clearance systems in the brain implications for Alzheimer disease," Nature Reviews Neurology 11(8), 2015, pp. 457-470.
Tyler, W., et al., "Remote Excitation of Neuronal Circuits Using Low-Intensity, Low-Frequency, Ultrasound," PLOS ONE vol. 3, Issue 10, 2008, e3511, 11 pages.
Westergard, T., et al., "Cell-to-Cell Transmission of Dipeptide Repeat Proteins Linked to C9orf72-ALS/FTD," Cell Reports, vol. 17, Issue 3, 2016, pp. 645-652.
Wray, S., et al., "Direct analysis of tau from PSP brain identifies new phosphorylation sites and a major fragment of N?terminally cleaved tau containing four microtubule?binding repeats," Journal of Neurochemistry, vol. 105, 2008, pp. 2343-2352.
Written Opinion of the International Preliminary Examining Authority for International Application No. PCT/US2019/042879, mailed Feb. 25, 2021 (6 pages).
Written Opinion of the International Preliminary Examining Authority for International Application No. PCT/US2019/042880, mailed Sep. 11, 2020 (8 pages).
Wszolek, Z., et al., "Frontotemporal dementia and parkinsonism linked to chromosome 17 (FTDP-17)" Orphanet Journal of Rare Diseases, 2006, 1:30, pp. 1-9.
Xie, L., et al., "Sleep Drives Metabolite Clearance from the Adult Brain," Science vol. 342, Issue 6156, 2013, pp. 373-377.
Zhang, Y., et al., "Aggregation-prone c9FTD/ALS poly(GA) RAN-translated proteins cause neurotoxicity by inducing ER stress," Acta Neuropathologica, vol. 128, 2014, pp. 504-524.
International Searching Authority, International Search Report for International Application No. PCT/US22/34706, dated Oct. 18, 2022, together with the Written Opinion of the International Searching Authority, 8 pages.
Extended European Search Report for European Application No. 19839881.0 dated Jun. 21, 2022, 9 pages.
Extended European Search Report for European Application No. 19840444.4 dated Jun. 28, 2022, 7 pages.
International Searching Authority, International Search Report for International Application No. PCT/US2022/037609, dated Oct. 26, 2022, together with the Written Opinion of the International Searching Authority, 8 pages.
Kim Kwang Soo, et al., "Proteolytic Cleavage of Extracellular a-Synuclein by Plasmin: Implications for Parkinson Disease" Journal of Biological Chemistry, vol. 287, No. 30, Mar. 22, 2012, pp. 24862-24872.
Mori, K., et al., "The C9orf72 GGGGCC repeat is translated into aggregating dipeptide-repeat proteins in FTLD/ALS," Science, vol. 339, No. 6125, Feb. 7, 2013, pp. 1335-1338.
Saido, T., et al., "Proteolytic Degradation of Amyloid 13-Protein" Cold Spring Harbor Perspectives in Medicine, vol. 2, No. 6, Jun. 1, 2012, pp. a006379-a006379.
Spencer, B., et al., "Lentivirus Mediated Delivery of Neurosin Promotes Clearance of Wild-type a-Synuclein and Reduces the Pathology in an a-Synuclein Model of LBD", Molecular Therapy, vol. 21, No. 1, Jan. 1, 2013, pp. 31-41.
Tanji, K., et al., "Proteinase K-resistant a-synuclein is deposited in presynapses in human Lewy body disease and A53T a-synuclein transgenic mice," Acta Neuropathologica, Springer, Berlin, DE, vol. 120, No. 2, Mar. 26, 2010, pp. 145-154.
Abbott, N., et al., "The role of brain barriers in fluid movement in the CNS: is there a 'glymphatic' system?" Acta Neuropathologica vol. 135, 2018, pp. 387-407.
Allen, J., et al., "Abstract 3483: Modeling circulating tumor cells in the peripheral blood and CSF of breast cancer patients," Cancer Research vol. 73, Issue 8, 2013, abstract only.
Allen, J., et al., "Abstract 5565: Circulating tumor cells in the peripheral blood and cerebrospinal fluid of patients with central nervous system metastases," Cancer Research vol. 72, Issue 8, 2012, abstract only.
Andersen, P., et al., "Clinical genetics of amyotrophic lateral sclerosis: what do we really know?" Nature Reviews Neurology, vol. 7, 2011, pp. 603-615.
Arai, T., et al., "Phosphorylated and cleaved TDP?43 in ALS, FTLD and other neurodegenerative disorders and in cellular models of TDP?43 proteinopathy," Neuropathology, vol. 30, 2010, pp. 170-181.
Arai, T., et al., "TDP-43 is a component of ubiquitin-positive tau-negative inclusions in frontotemporal lobar degeneration and amyotrophic lateral sclerosis," Biochemical and Biophysical Research Communications, vol. 351, Issue 3, 2006, pp. 602-611.
Arriagada, P., et al., "Neurofibrillary tangles but not senile plaques parallel duration and severity of Alzheimer's disease," Neurology 42, 1992, pp. 631-639.
Asai, D., et al., "Chapter 3 Making Monoclonal Antibodies," Methods in Cell Biology, vol. 37, 1993, pp. 57-74.
Bioline "Proteinase K" accessed from bioline.com on Jun. 22, 2021 (Year: 2013).
Brat, D., et al., "Tau?associated neuropathology in ganglion cell tumours increases with patient age but appears unrelated to ApoE genotype," Neuropathy and Applied Neurobiology, vol. 27, Issue 3, 2001, pp. 197-205.
Buee, L., et al., "Tau protein isoforms, phosphorylation and role in neurodegenerative disorders," Brain Research Reviews, vol. 33, Issue 1, 2000, pp. 95-130.
Chang, Y., et al., "The Glycine-Alanine Dipeptide Repeat from C9orf72 Hexanucleotide Expansions Forms Toxic Amyloids Possessing Cell-to-Cell Transmission Properties" Journal of Biological Chemistry, vol. 291, Issue 10, 2016, pp. 4903-4911.
Coatti, G., et al., "Pericytes Extended Survival of Als SOD1 Mice and Induce the Expression of Antioxidant Enzymes in the Murine Model and in IPSCs Dervised Neuronal Cells from an ALS Patient," Stem Cell Reviews and Reports (2017) 13: 686-698.
De Souza, P., et al., "A biotechnology perspective of fungal proteases," Brazilian Journal of Microbiology, vol. 46, 2, 2015, pp. 337-346.
Dejesus-Hernandez, M., et al., "Expanded GGGGCC Hexanucleotide Repeat in Noncoding Region of C9ORF72 Causes Chromosome 9p-Linked FTD and ALS," Neuron, vol. 72, 2011, pp. 245-256.
Diamond, S., "Methods for mapping protease specificity," Current Opinion in Chemical Biology, vol. 11, Issue 1, 2007, pp. 46-51.
Evidente, V., et al., "Post-encephalitic parkinsonism,"Journal of Neurology, Neurosurgery & Psychiatry, vol. 63, Issue 1, 1998, pp. 5.
Finsterer, J., et al., "Liquorpheresis (CSF filtration) in familial amyotrophic lateral sclerosis," Spinal Cord, vol. 39, 1999, pp. 592-593.
Giannakopoulos, P., et al., Tangle and neuron Nos., but not amyloid load, predict cognitive status in Alzheimer's disease, Neurology, vol. 60, 2003, pp. 1495-1500.
Giordana, M., et al., " Dementia and cognitive impairment in amyotrophic lateral sclerosis: a review," Neurological Sciences, vol. 32, 2011, pp. 9-16.
Gomez-Isla, T., et al., Neuronal loss correlates with but exceeds neurofibrillary tangles in Alzheimer's disease, Annals of Neurology, vol. 41, 1997, pp. 17-24.

(56) References Cited

OTHER PUBLICATIONS

Grad, L., et al., "Prion-like activity of Cu/Zn superoxide dismutase: implications for amyotrophic lateral sclerosis," 8:1, 2014, pp. 33-41.
Graff-Radford, N., et al., "Frontotemporal dementia," Seminars in Neurology vol. 27, 2007, pp. 48-57.
Hasegawa, M., et al., "Molecular Dissection of TDP-43 Proteinopathies," Journal of Molecular Neuroscience, vol. 45, 2011, pp. 480-485.
Hasegawa, M., et al., "Phosphorylated TDP-43 in frontotemporal lobar degeneration and amyotrophic lateral sclerosis," Annals of Neurology, vol. 62, Issue 1, 2008, pp. 60-70.
Hersh, D., et al., "MR-guided transcranial focused ultrasound safely enhances interstitial dispersion of large polymeric nanoparticles in the living brain," PLOS ONE 13(2): e0192240, 2018, 19 pages.
Indivero, V., "Technique filters cancer where chemo can't reach: A new therapy may help cancer patients with malignant ce4lls near the spinal cord and in the brain," dated Jul. 30, 2013. Retrieved from the internet under https://news.psu.edu/story/282970/2013/07/30/research/technique-filters-cancer-where-chemo-cant-reach, 4 pages.
International Preliminary Report on Patentability for International Application No. PCT/US2019/042880, mailed Jan. 21, 2021 (8 pages).
International Preliminary Report on Patentability for International Application No. PCT/US2020/027683, mailed Oct. 21, 2021 (11 pages).
International Search Report and Written Opinion for International Application No. PCT/US2019/042879, mailed Oct. 8, 2019 (14 pages).
International Search Report and Written Opinion for International Application No. PCT/US2019/042880, mailed Oct. 16, 2019 (10 pages).
International Search Report and Written Opinion for International Application No. PCT/US2020/027683, mailed Aug. 6, 2020 (19 pages).
International Search Report and Written Opinion for International Application No. PCT/US2021/013458, mailed Jun. 9, 2021 (20 pages).
International Search Report and Written Opinion for International Application No. PCT/US2021/052735, mailed Feb. 11, 2022, 28 pages.
International Search Report and Written Opinion for International Application No. PCT/US2021/053829 mailed Jan. 13, 2022 (120902-10902). 19 pages.
Jessen, N., et al., "The Glymphatic System—A Beginner's Guide," Neurochemical Research, 2015, 40(2), pp. 2583-2599.
Kaufman, S., et al., "Prion-Like Propagatio of Protein Aggregation and Related Therapeutic Strategies," Neurotherapeutics, 10, 2013, pp. 371-382.
Kopeikina, K., et al., "Soluble forms of tau are toxic in Alzheimer's disease," Translational Neuroscience 3(3), 2012. pp. 223-233.
Kouzehgarani, G., et al., "Harnessing cerebrospinal fluid circulation for drug delivery to brain tissues," Advanced Drug Delivery Reviews, 2021, vol. 173, pp. 20-59.
Lee, V., et al., "Neurodegenerative tauopathies," Annual Review of Neuroscience, vol. 24, 2001, pp. 1121-1159.
Legon, W., et al., "Transcranial focused ultrasound modulates the activity of primary somatosensory cortex in humans," Nature Neuroscience vol. 17, No. 2, 2014, pp. 322-329.
Lei, P., et al., "Tau protein: relevance to Parkinson's disease," The International Journal of Biochemistry & Cell Biology, vol. 42, Issue 11, 2010, pp. 1775-1778.
Lin et al., "Facile synthesis of enzyme—inorganic hybrid nanoflowers and their application as an immobilized trypsin reactor for highly efficient protein digestion." (Communication) RSC Adv., 2014, 4, 13888-13891.
Lin, Z., et al., "Facile synthesis of enzyme—inorganic hybrid nanoflowers and their application as an immobilized trypsin reactor for highly efficient protein digestion." (Communication) RSC Adv., 2014, 4, 13888-13891.
Lipsman, N., et al., "Blood-brain barrier opening in Alzheimer's disease using MR-guided focused ultrasound," Nature Communications vol. 9, Article 2336, 2018, pp. 1-8.
Lomen-Hoerth, C., et al., "The overlap of amyotrophic lateral sclerosis and frontotemporal dementia," Neurology, vol. 59, 2002, pp. 1077-1079.
Martin, L., et al., "Post-translational modifications of tau protein: implications for Alzheimer's disease," Neurochemistry International, vol. 58, Issue 4, pp. 458-471.
Marx, S., et al., "Bench to Bedside: The Development of Rapamycin and Its Application to Stent Restenosis", Journal of the American Heart Association 104, 2001, pp. 852-855.
May, S., et al., "C9orf72 FTLD/ALS-associated Gly-Ala dipeptide repeat proteins cause neuronal toxicity and Unc119 sequestration," Acta Neuropathologica, vol. 128, 2014, pp. 485-503.
Mckee, A., et al., "The Neuropathology of Chronic Traumatic Encephalopathy," Brain Pathology 253), 2015, pp. 350-364.
Chinese Office Action for Chinese Application No. 202080041867.5, dated Jul. 12, 2023 (12 pages).
Extended European Search Report for European Patent Application No. 20788080.8, dated Jun. 4, 2024 (12 pages).
International Preliminary Report on Patentability for International Application No. PCT/US2022/034706 mailed Jan. 4, 2024 (7 pages).
International Search Report and Written Opinion for International Application No. PCT/US2023/015972, mailed Jul. 27, 2023, 12 pages.
International Search Report and Written Opinion for International Application No. PCT/US23/17893, mailed Jun. 29, 2023 (13 pages).
International Searching Authority, International Search Report for International Application No. PCT/US2024/017736, dated Aug. 19, 2024, together with the Written Opinion of the International Searching Authority, 15 pages.
Notice of Reasons for Refusal for Japanese Patent Application No. 2021-560113, with English translation, dated Jan. 4, 2024 (12 pages).
Office Action Decision of Refusal from Japanese Patent Office for application No. 2021-560113 dated Jun. 25, 2024, 5 pages.
Second Chinese Office Action for Chinese Patent Application No. 202080041867.5, with English translation, dated Apr. 30, 2024 (26 pages).
Extended European Search Report for European Patent Application No. 22829302.3 dated May 28, 2025, 9 pages.

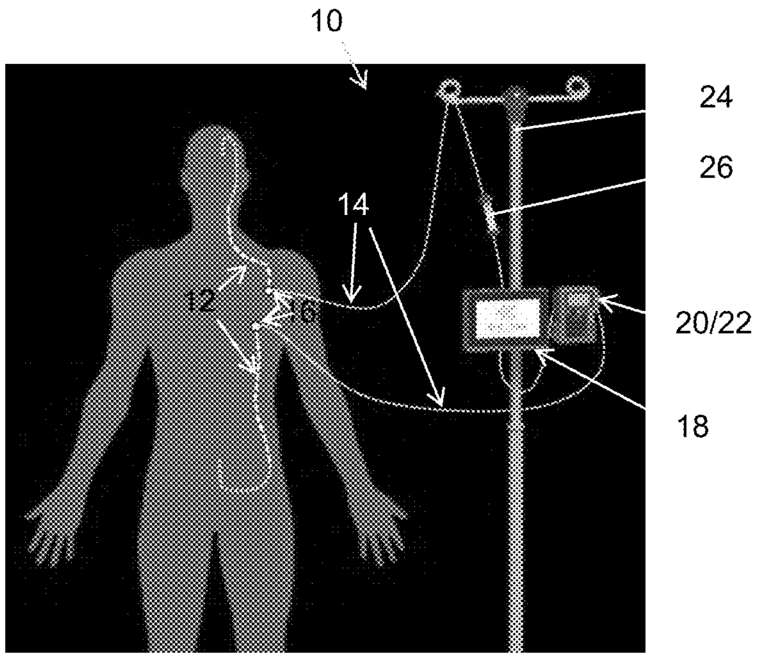
Figure 1A: CSF Circuit
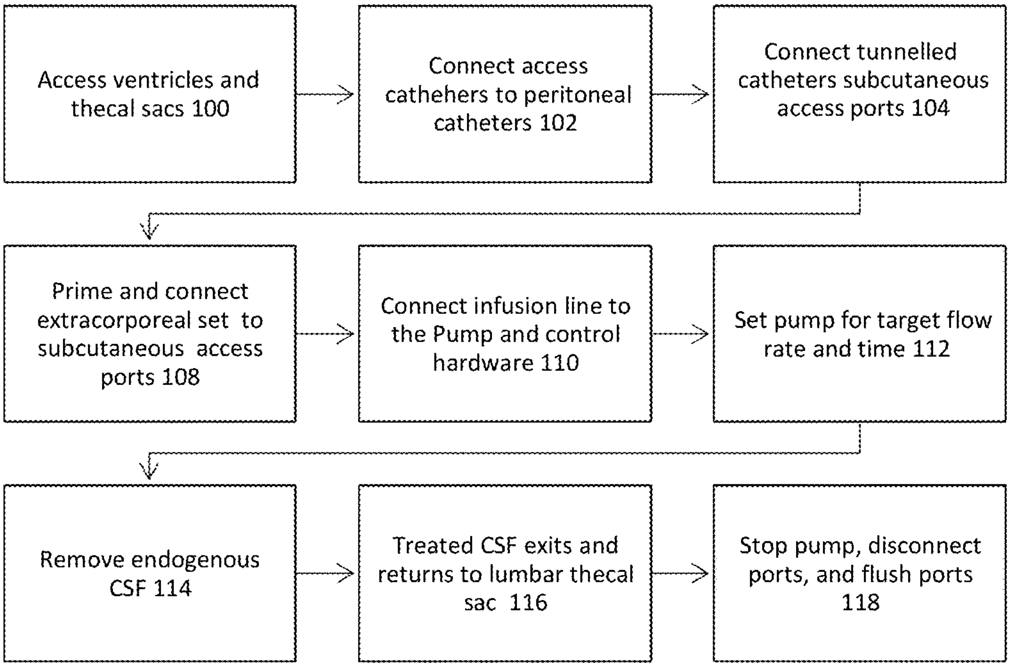
Figure 1C: High-level surgical flow

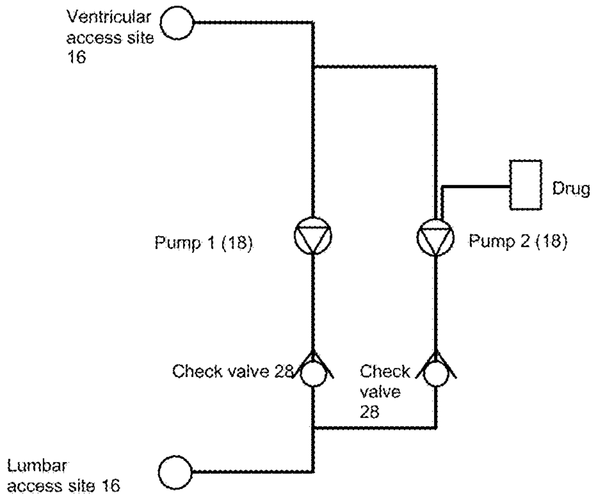
*Figure 2: Two pump circuit with drug fed into pump through separate fluid line*
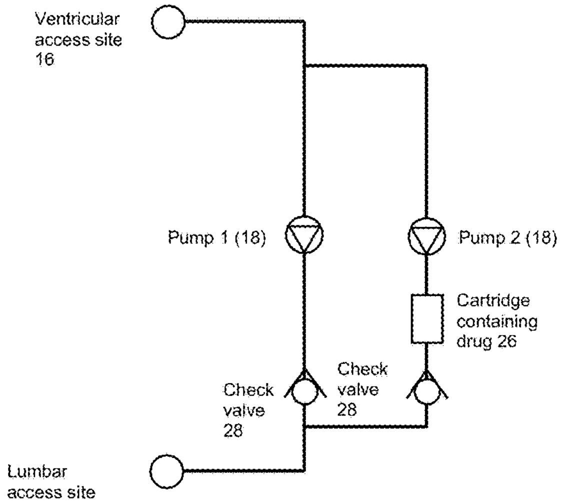
*Figure 3: Two pump circuit with drug introduced directly into fluid line*
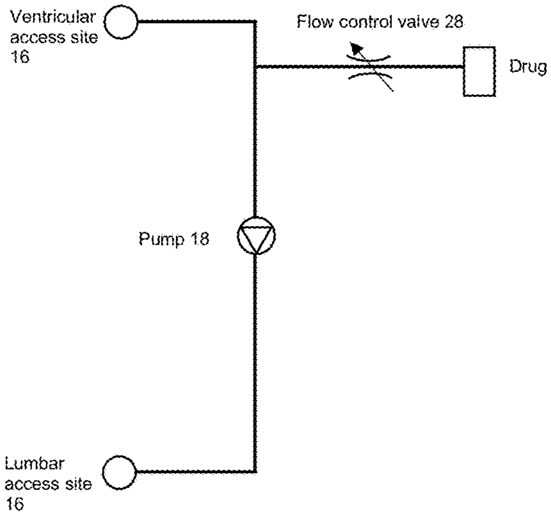
*Figure 4A: Flow control valve circuit*

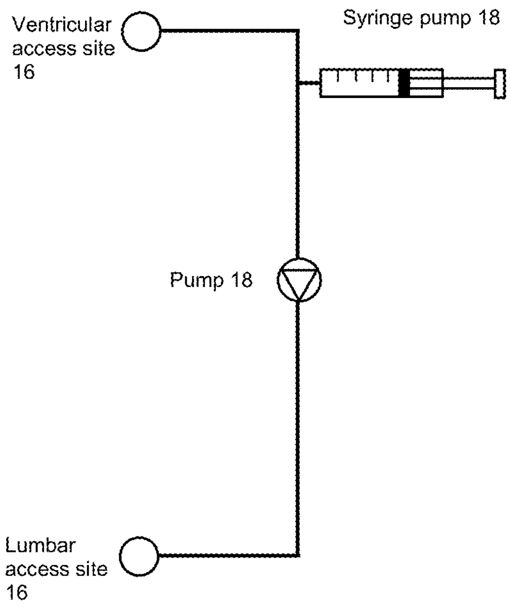
*Figure 4b: Syringe pump dosing circuit*

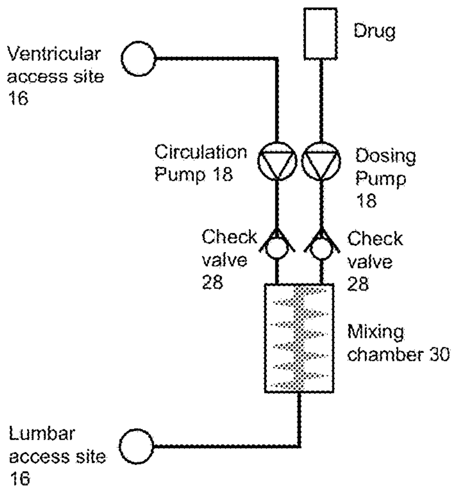
*Figure 5: Two-pump circuit with mixing chamber*
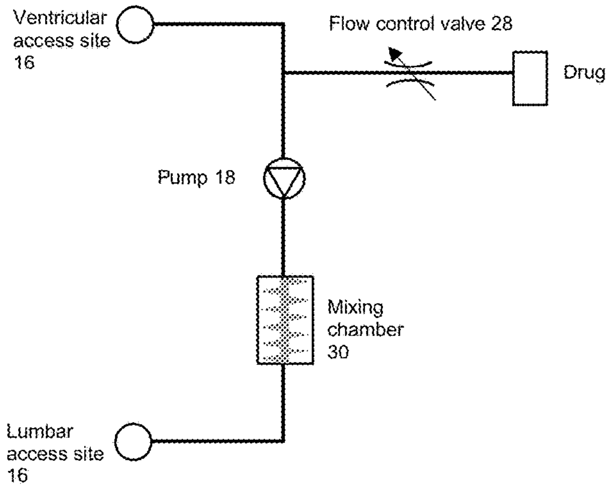
*Figure 6: Flow control valve circuit with mixing chamber*
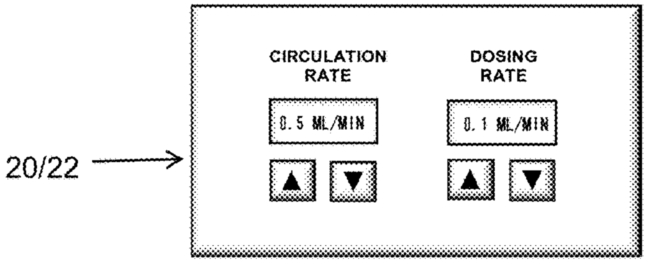
*Figure 7: System interface with controls for circulation rate of CSF and dosing rate of drug*
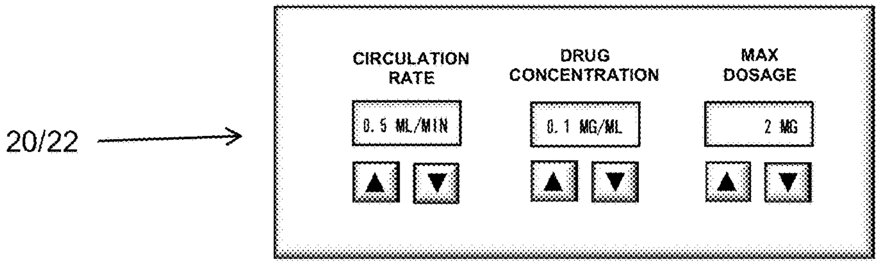
*Figure 8. System interface with controls for circulation rate of CSF, target drug concentration in CSF, and max dosage of drug*

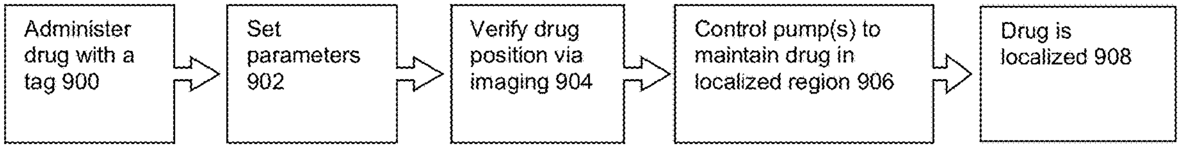
*Figure 9: Method of localizing drug to target area of brain*
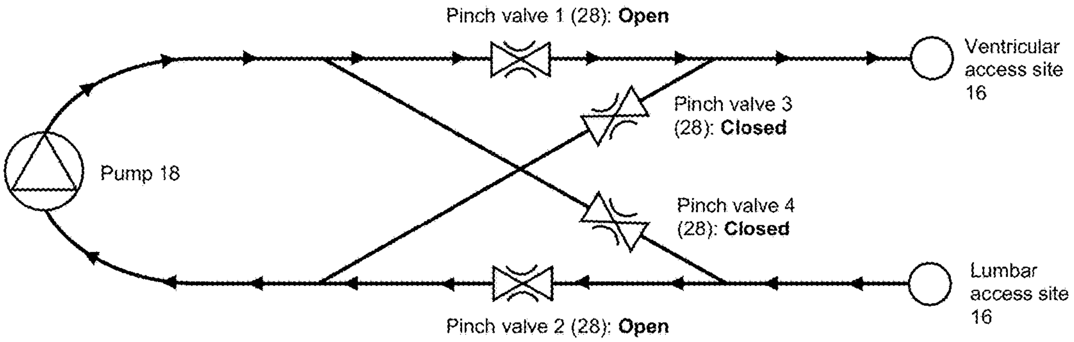
*Figure 10: Directing flow from lumbar to ventricle*
To direct flow from ventricle to lumbar:
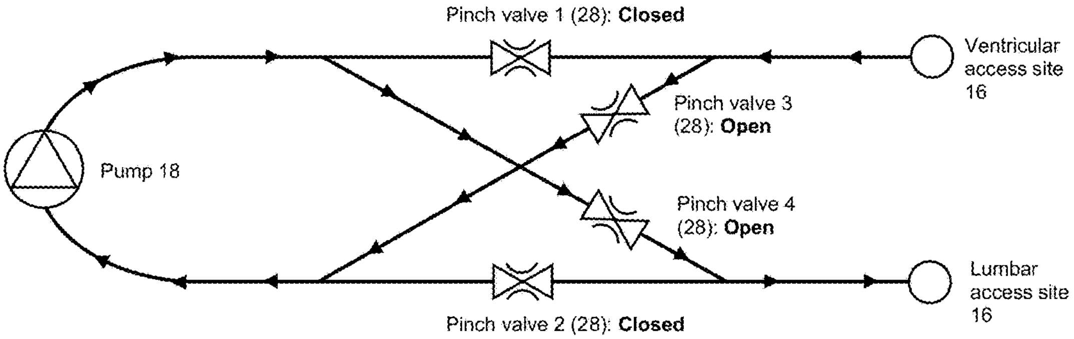
*Figure 11: Directing flow from ventricle to lumbar*

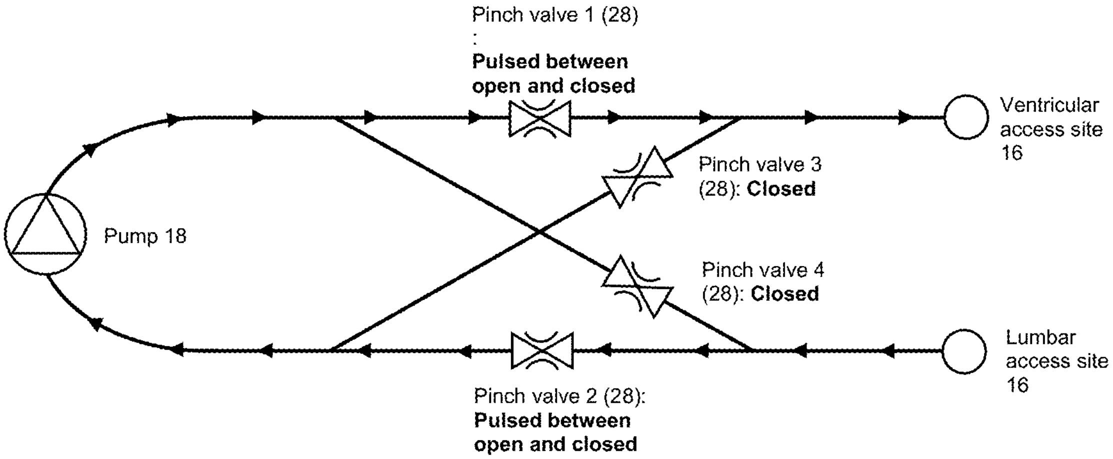
*Figure 12: Flowing from lumbar to ventricle with a pulsatile flow pattern*
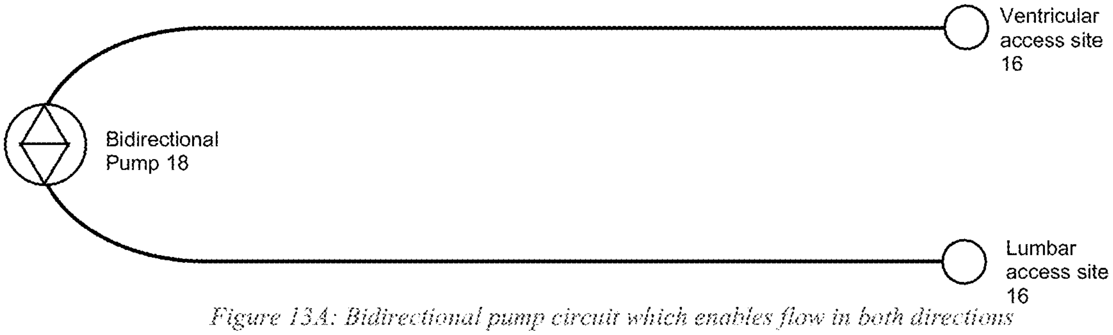
*Figure 13A: Bidirectional pump circuit which enables flow in both directions*

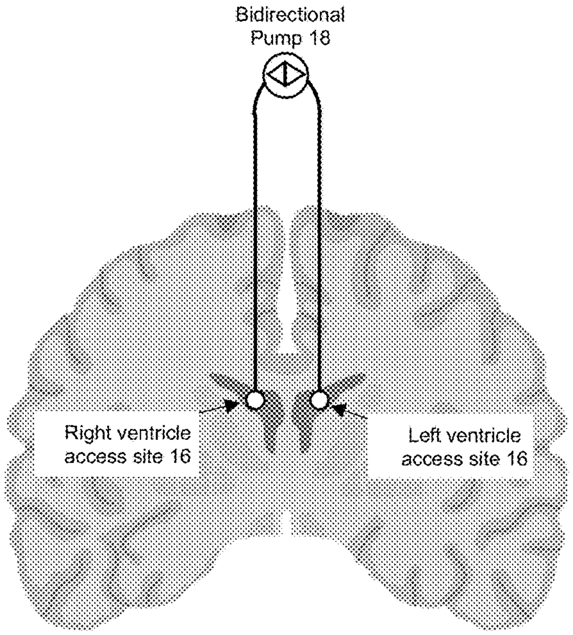
*Figure 13B: Bidirectional pump circuit which enables flow in both directions between right and left ventricles in the brain*
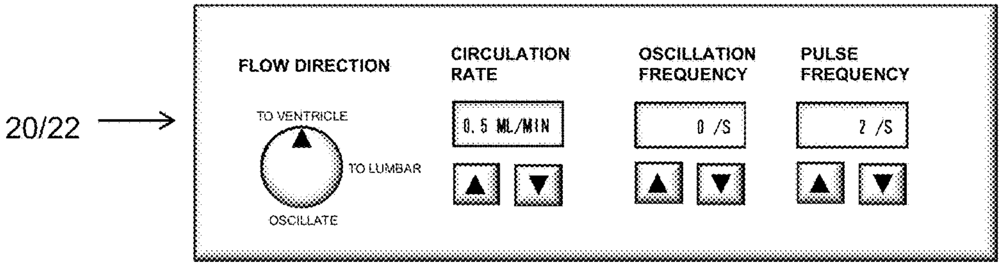
*Figure 14: System interface with controls for flow direction of CSF, circulation rate, frequency of oscillations between flow directions, and pulse frequency*

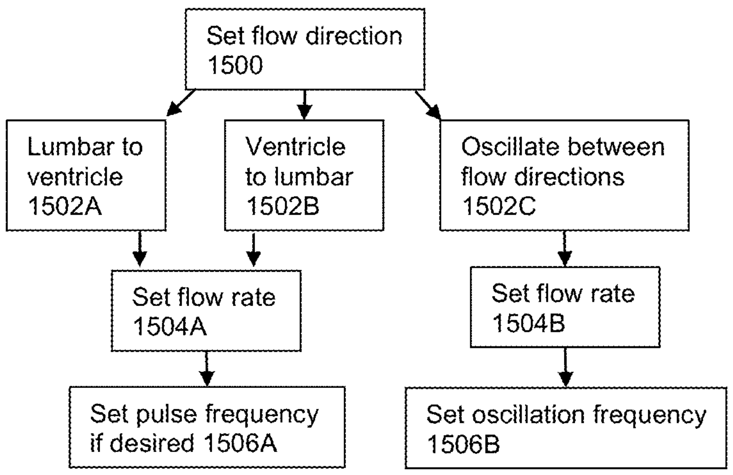
*Figure 15: Method to manually program method of delivery*

A

B

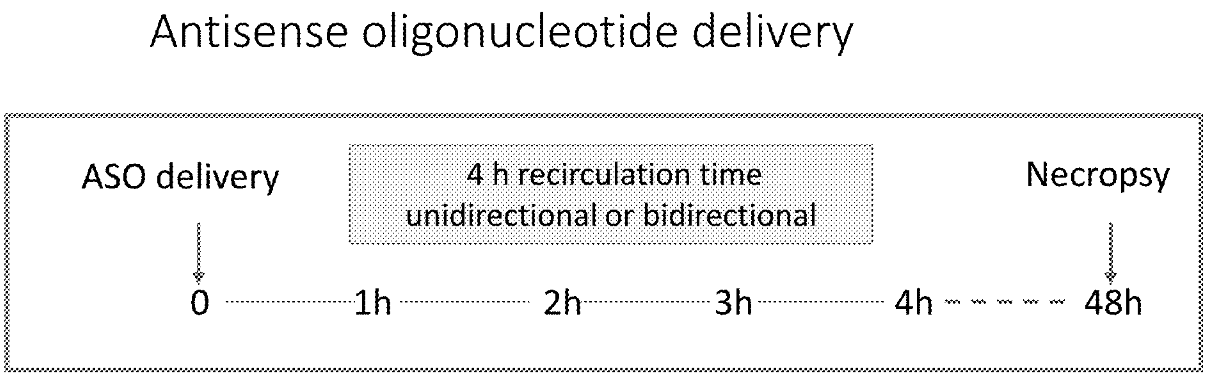
*Figure 17A: Schema of in-vivo study*
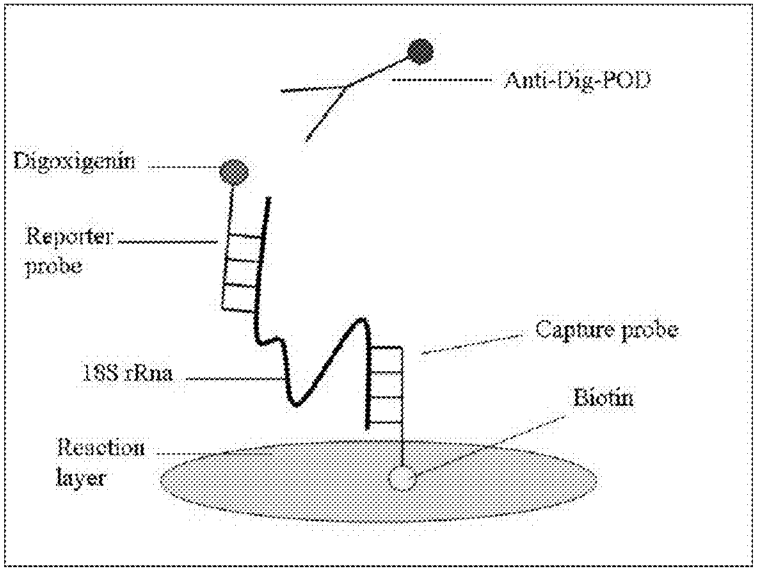
*Figure 17B: Detection method for ASO*

*Figure 17C. Tissue levels after Unidirectional or Bidirectional recirculation of ASO*
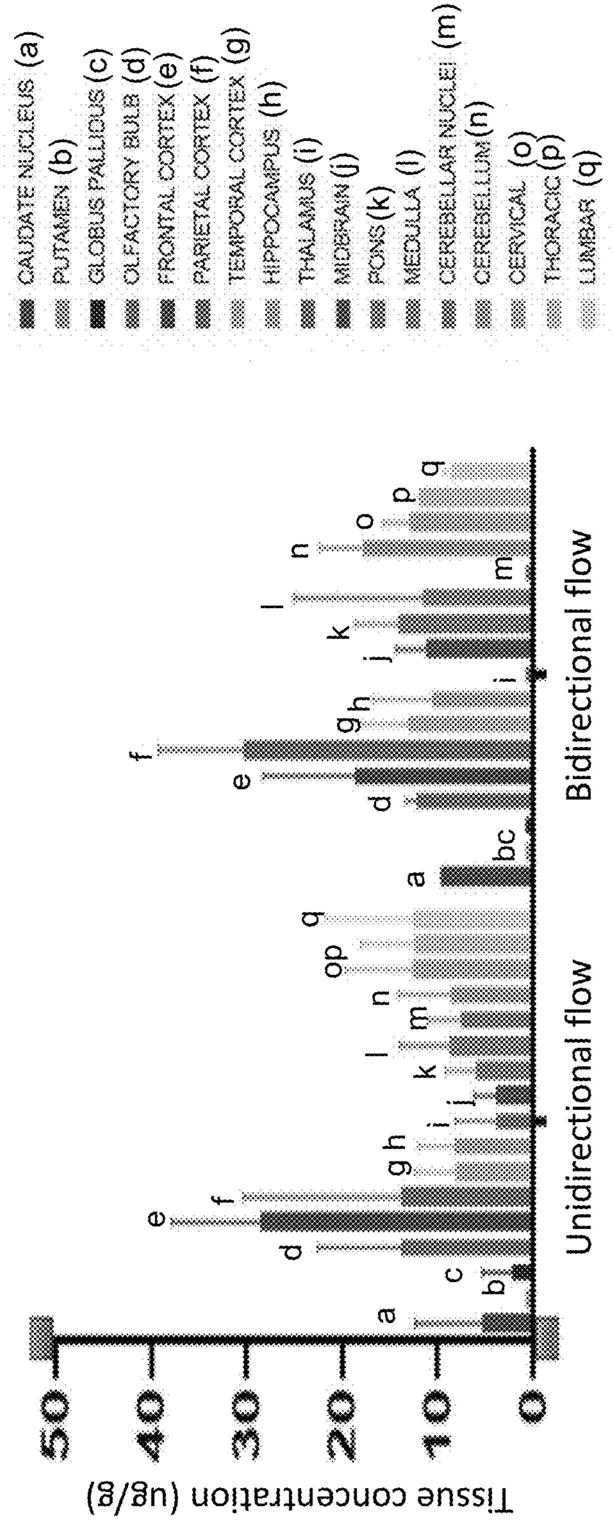

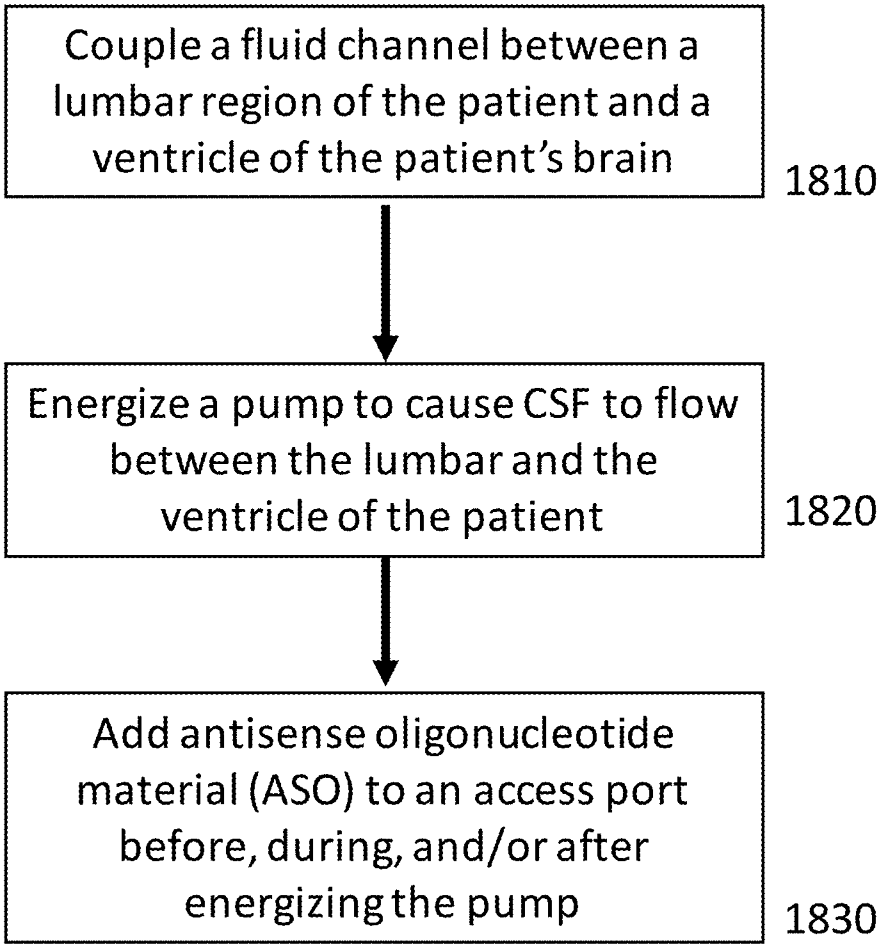
*Figure 18. Method of Regulating Gene Expression of a Patient*

METHOD OF REGULATING GENE EXPRESSION

PRIORITY

This patent application claims priority from Provisional U.S. Patent Application No. 63/214,239, filed Jun. 23, 2021, entitled, "FLUID MANAGEMENT SYSTEM," and naming Gianna N. Riccardi, Marcie Glicksman, Anthony DePasqua, Kevin Kalish, Rajan Patel, and Alan Watson as inventors.

This application is also a Continuation-In-Part of U.S. patent application Ser. No. 17/489,620 filed on Sep. 29, 2021, and entitled, "SUBARACHNOID FLUID MANAGEMENT METHOD AND SYSTEM WITH VARYING RATES," which claims the benefit of, and priority to, U.S. provisional patent application No. 63/084,996, filed Sep. 29, 2020, and U.S. provisional patent application No. 63/117,975, filed Nov. 24, 2020.

This application is also a Continuation-In-Part of U.S. patent application Ser. No. 17/495,682, filed on Oct. 6, 2021, and entitled, "SYSTEM AND METHOD FOR CONTROLLING CSF FLOW AND MANAGING INTRACRANIAL PRESSURE," which claims the benefit of, and priority to, U.S. provisional patent application No. 63/088,401, filed Oct. 6, 2020.

This application is also a Continuation-In-Part of U.S. patent application Ser. No. 17/669,883 filed on Feb. 11, 2022, and entitled "METHODS OF AMELIORATION OF CEREBROSPINAL FLUID AND DEVICES AND SYSTEMS THEREFOR," which is a continuation of U.S. patent application Ser. No. 17/062,440, filed on Oct. 2, 2020, which is a continuation of PCT Patent Application Number PCT/US20/27683, filed on Apr. 10, 2020, which claims priority to and the benefit of U.S. Provisional Patent Application No. 62/832,486, filed on Apr. 11, 2019, and U.S. Provisional Patent Application No. 62/960,861, filed on Jan. 14, 2020.

The disclosures of all of the above noted patent applications are incorporated herein by reference in their entireties, including the drawings and appendices.

GOVERNMENT RIGHTS

None

FIELD

Illustrative embodiments generally relate to medical devices and methods and, more particularly, illustrative embodiments relate to devices and methods for managing subarachnoid fluid, such as cerebrospinal fluid ("CSF"), and/or drug delivery that may be used to treat neurodegenerative disorders.

BACKGROUND

When delivering a drug intrathecally, it is difficult to ensure that the delivered dosage reaches the target anatomy (e.g., part of the brain correlating to a specific disease, such as the cortical versus subcortical). It also is difficult to verify the actual dosage delivered to the target anatomy, as well as control, in real time, the concentration of the drug in the fluid surrounding the target anatomy.

SUMMARY OF VARIOUS EMBODIMENTS

In accordance with one embodiment of the invention, a method of regulating gene expression of a patient couples a fluid channel between the lumbar region of the patient and the ventricle of the patient's brain. The fluid channel fluidly connects the lumbar region and the ventricle, and the fluid channel has an access port and a pump. The pump is energized to cause CSF to flow between the lumbar and ventricle of the patient. Antisense oligonucleotide material (ASO) is added to the access port before, during, and/or after energizing the pump.

The method may further include de-energizing the pump to cause the CSF to flow under natural flow processes. The CSF may flow in one direction only between energizing and de-energizing the pump.

The method may further de-energize the pump to cause the CSF to flow under natural flow processes. The CSF may flow in two or more directions between energizing and de-energizing the pump.

The method may further reverse the direction of the pump output to cause the ASO to pass by the same point in the ventricle or lumbar regions in two directions. The fluid channel may further include a catheter having a lumen configured to transport ASO mixed with CSF of the patient. Adding antisense oligonucleotide material may include adding a bolus of antisense oligonucleotide material to the fluid channel through the access port.

The method may further include controlling, via a controller, the pump output rate as a function of a parameter of the patient. The fluid channel may form a closed loop configured to circulate CSF and ASO mixture through the ventricle, the body chambers through which CSF flows, the lumbar, and fluid channel in one or two directions. The fluid channel may include a catheter.

Coupling a fluid channel between the lumbar region of the patient and the ventricle may include locating a lumbar catheter in-vivo to the patient and extending from the patient's lumbar, locating a ventricle catheter in-vivo to the patient and extending from the patient's ventricle, mechanically coupling the catheter to the lumbar catheter, mechanically coupling the catheter to the ventricle catheter, and mechanically coupling the to the lumbar and ventricle catheters fluidly coupling the lumbar and ventricle of the patient via the fluid channel.

In accordance with another embodiment, a kit configured to assist with regulating gene expression includes an antisense oligonucleotide material (ASO) and a fluid management circuit. The fluid management circuit includes a pump, a catheter having an internal lumen, an access port configured to facilitate addition of ASO to the internal lumen of the catheter, and mechanical couplings configured to couple the catheter between and with at least two spaced apart internal catheters. The pump may be configured to selectively flow in either of two directions. The kit may further include a controller configured for controlling the pump output.

In accordance with another embodiment, a method of regulating gene expression of a patient includes providing fluid management system comprising a pump, a catheter, and an access port that is either part of the catheter or separate from the catheter. The method includes securing together the pump, catheter and access port to form a CSF fluid channel, coupling the catheter to an internal lumbar catheter extending from and embedded within the patient's the lumbar region, coupling another end of the catheter to an internal ventricle catheter extending from and embedded within the patient's the ventricle region, energizing the pump to cause CSF to flow in one or two opposite directions between the lumbar region and ventricle region of the patient; and adding antisense oligonucleotide material (ASO) to the catheter through the access port before, during, and/or after energizing the pump.

The method may further include de-energizing the pump to cause the CSF to flow under natural flow processes. The CSF may flow in one direction only between energizing and de-energizing the pump.

The method may further include de-energizing the pump to cause the CSF to flow under natural flow processes. The CSF may flow in two or more directions between energizing and de-energizing the pump.

The method may further include reversing the direction of the pump output to cause the ASO to pass by the same point within the ventricle or lumbar region in two directions. The catheter may form a closed loop configured to circulate CSF and ASO mixture through the ventricle, the body chambers through which CSF flows, and the lumbar in one or two directions.

Adding antisense oligonucleotide material may include adding a bolus of antisense oligonucleotide material to the catheter through the access port.

Adding antisense oligonucleotide material may include adding a gradual flow of antisense oligonucleotide material to the catheter through the access port.

The method may further include controlling, via a controller, the pump to oscillate CSF fluid flow.

Illustrative embodiments of the invention are implemented as a computer program product having a computer usable medium with computer readable program code thereon. The computer readable code may be read and utilized by a computer system in accordance with conventional processes.

BRIEF DESCRIPTION OF THE DRAWINGS

Those skilled in the art should more fully appreciate advantages of various embodiments of the invention from the following "Description of Illustrative Embodiments," discussed with reference to the drawings summarized immediately below.

FIG. 1A schematically shows a cerebrospinal fluid circuit that may be used with illustrative embodiments of the invention.

FIG. 1C shows a high level surgical flow process in accordance with illustrative embodiments of the invention.

FIG. 2 schematically shows a two pump circuit with drug fed into pump through separate fluid line in accordance with illustrative embodiments.

FIG. 3 schematically shows a two pump circuit with drug introduced directly into fluid line FIG. 4A schematically shows a flow control valve circuit that may be used with illustrative embodiments.

FIG. 4B schematically shows a syringe pump dosing circuit with a drug introduced directly into the fluid line configured and usable with illustrative embodiments.

FIG. 5 schematically shows a two-pump circuit with a mixing chamber in accordance with illustrative embodiments.

FIG. 6 schematically shows a flow control valve with a mixing chamber in accordance with other embodiments.

FIGS. 7 and 8 schematically show two different user interfaces in accordance with illustrative embodiments.

FIG. 9 shows a process of localizing drug delivery to a target area of the brain in accordance with illustrative embodiments.

FIG. 10 schematically shows directing flow from lumbar to ventricle in accordance with illustrative embodiments.

FIG. 11 schematically shows directing flow from ventricle to lumbar in accordance with illustrative embodiments.

FIG. 12 schematically shows directing flow from lumbar to ventricle with a pulsatile pattern in accordance with illustrative embodiments.

FIGS. 13A and 13B schematically show bidirectional pump circuits that enable flow in two opposite directions (FIG. 13B between right and left ventricles in the brain) in accordance with illustrative embodiments.

FIG. 14 schematically shows another system interface in accordance with illustrative embodiments.

FIG. 15 shows a process of manually programming drug delivery in accordance with illustrative embodiments.

FIGS. 17A, 17B, and 17C detail another example of illustrative embodiments of the invention.

FIG. 18 shows a method of regulating gene expression of a patient in accordance with illustrative embodiments.

DESCRIPTION OF ILLUSTRATIVE EMBODIMENTS

Figure 1B:
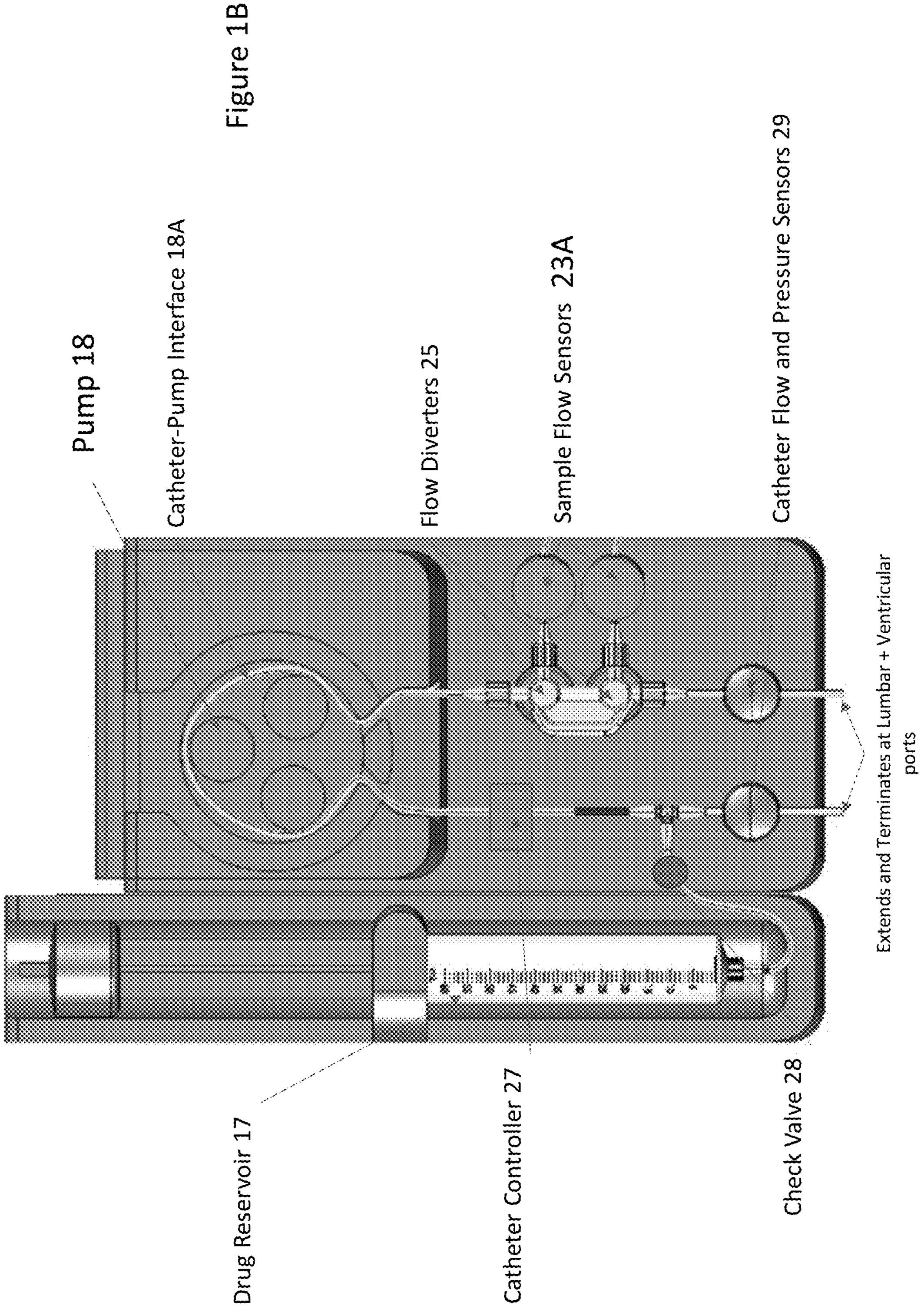
FIG. 1B schematically shows an external catheter configured in accordance with illustrative embodiments.

Illustrative embodiments regulate patient gene expression by controllably circulating antisense oligonucleotide material (ASO) through a closed fluid circuit formed between the patient's ventricle and lumbar regions. To that end, after coupling a fluid channel between those regions, such embodiments add ASO to the fluid channel (preferably after the channel is primed with CSF) and energize a pump to controllably flow the CSF and the ASO mixed with the CSF. CSF/ASO fluid flow may be managed to localize treatment (e.g., providing deep brain distribution) while minimizing toxicity potentially caused by the ASO to certain nerves (e.g., the peripheral nerve). Details of various embodiments are discussed below.

In additional illustrative embodiments, a system controllably applies a therapeutic material, such as a drug (e.g., methotrexate, a chemotherapy, small interfering RNA (siRNA), microRNA (miRNA), plasmid DNA, messenger RNA (mRNA), small activating RNA (saRNA), splicing-modulatory ASOs, and CRISPR (clustered regularly interspaced short palindromic repeats)/Cas (CRISPR-associated protein, adenoviral vectors (AAV), and immunosuppressive drug) to a specific anatomical location within the subarachnoid space or other area. The therapeutic material, which also may be referred to herein as a "drug," may be applied in a single large volume as a bolus, or dosed gradually over a longer time. To that end, the system has a controller or control system that manages distribution of the therapeutic material within a CSF circuit through which cerebrospinal fluid ("CSF") flows. Specifically, among other things, the controller (or "control system") manages pumps, valves, catheters, and/or other structure(s) to control fluid flow, flow direction, and frequencies of certain periodic flows of bodily fluids (e.g., CSF), to provide a more localized and efficient therapeutic application to a patient.

Preferred embodiments enable the therapeutic material to penetrate the blood-brain barrier by either selecting appropriate CSF and therapeutic material flow rates, and/or controlling CSF flow to maintain a bolus of the therapeutic material within CSF at/near a desired location in the CSF circuit. Consequently, using various embodiments, medical practitioners can be more comfortable applying the appropriate application of the therapeutic in the patient, while reducing toxicity and, in some cases, reducing the need for larger volumes of the therapeutic. Details of illustrative embodiments are discussed below.

Many neurodegenerative diseases have been tied to the accumulation of biomolecules (e.g., toxic proteins) contained in cerebrospinal fluid (CSF) or other fluids (e.g., interstitial fluid) within the subarachnoid space (SAS) of a mammalian subject. Problematically, these (e.g., toxic) biomolecules may be secreted and then transported by the CSF to other cells in the body, which process may occur over the span of years. For example, dipeptide repeat proteins (DPRs) and/or TDP-43 have been implicated in neuronal death in the pathology of amyotrophic lateral sclerosis (ALS, or Lou Gehrig's disease), Alzheimer disease (AD), frontotemporal degeneration (FTD), Parkinson's disease (PD), Huntington's disease (HD), and progressive supranuclear palsy (PSP), to name just a few. Hence, research has focused primarily on the removal of harmful DPRs. Techniques for removing DPRs and/or TDP-43 have included: shunting CSF from the CSF space, diluting the CSF (e.g., with an artificial fluid), administering a drug into the CSF, conditioning the CSF, and/or manipulating CSF flow.

Recent breakthrough techniques for handling this problem include ameliorating the CSF, and treating a neurological disorder by removing or degrading a specific (toxic) protein.

Amelioration, as used in various embodiments, involves systems and methods for ameliorating a fluid in the subarachnoid space (SAS) (e.g., a cerebrospinal fluid (CSF), an interstitial fluid (ISF), blood, and the like) of a mammalian subject, unless otherwise particularly distinguished (e.g., referred to as solely CSF). Representative systems may be completely or partially implanted within the body of the mammalian subject (discussed below). Within the body, the systems and/or components thereof may also be completely or partially implanted within the SAS and exposed to the exterior via a port 16 (e.g., a medical valve that provides selective access to the interior system components). These systems execute processes that may occur entirely in-vivo, or some steps that occur extracorporeally. Illustrative embodiments ameliorate with a CSF circuit, discussed below.

Amelioration, for the purpose of illustration, may include changing the physical parameters of the fluid, as well as digestion, removal, immobilization, reduction, and/or alteration, to become more acceptable and/or inactivation of certain entities, including: target molecules, proteins, agglomerations, viruses, bacteria, cells, couples, enzymes, antibodies, substances, and/or any combination thereof. For example, in some embodiments and applications, amelioration may refer to removing toxic proteins from or conditioning one or more of the blood, interstitial fluid, or glymph contained therein, or other fluid, as well as the impact that this removal has on treating diseases or conditions that affect various bodily functions, (i.e., improving the clinical condition of the patient). Moreover, amelioration may be performed by any one of: digestion, enzymatic digestion, filtration, size filtration, tangential flow filtering, countercurrent cascade ultrafiltration, centrifugation, separation, magnetic separation (including with nanoparticles and the like), electrophysical separation (performed by means of one or more of enzymes, antibodies, nanobodies, molecular imprinted polymers, ligand-receptor complexes, and other charge and/or bioaffinity interactions), photonic methods (including fluorescence-activated cell sorting (FACS), ultraviolet (UV) sterilization, and/or optical tweezers), photoacoustical interactions, chemical treatments, thermal methods, and combinations thereof. Advantageously, various embodiments or implementations of the present invention may reduce levels of toxicity and, after reduced, facilitate maintaining the reduced levels over time.

The extent of amelioration, as reflected by the concentration of the target biomolecules, may be detected through a variety of means. These include optical techniques (e.g., Raman, coherent Stokes, and anti-Stokes Raman spectroscopy; surface enhanced Raman spectroscopy; diamond nitrogen vacancy magnetometry; fluorescence correlation spectroscopy; dynamic light scattering; and the like) and use of nanostructures such as carbon nanotubes, enzyme linked immunosorbent assays, surface plasmon resonance, liquid chromatography, mass spectrometry, circular proximity ligation assays, and the like.

Amelioration may include the use of a treatment system (e.g., UV radiation, IR radiation), as well as a substance, whose properties make it suitable for amelioration. Amelioration of CSF or ameliorated CSF—which terms may be used interchangeably herein—refers to a treated volume of CSF in which one or more target compounds have been partially, mostly, or entirely removed. It will be appreciated that the term removed, as used herein, can refer not only to spatially separating, as in taking away, but also effectively removing by sequestering, immobilizing, or transforming the molecule (e.g., by shape change, denaturing, digestion, isomerization, or post-translational modification) to make it less toxic, non-toxic or irrelevant.

The term, "ameliorating agent" generally refers to a material or process capable of ameliorating a fluid, including enzymes, antibodies, or antibody fragments, nucleic acids, receptors, anti-bacterial, anti-viral, anti-DNA/RNA, protein/amino acid, carbohydrate, enzymes, isomerases, compounds with high-low biospecific binding affinity, aptamers, exosomes, ultraviolet light, temperature change, electric field, molecular imprinted polymers, living cells, and the like. Additional details of amelioration are taught by PCT Application No. PCT/US20/27683, filed on Apr. 10, 2020, the disclosure of which is incorporated herein, in its entirety, by reference. In a similar manner, details for further treatments are taught by PCT Application No. PCT/US19/042880, filed Jul. 22, 2019, the disclosure of which is incorporated herein, in its entirety, by reference.

To control CSF flow within the body (e.g., through the ventricle), illustrative embodiments form a CSF circuit/channel (identified by reference number "10") that manages fluid flow in a closed loop. FIG. 1A, for example, shows one embodiment of such a CSF circuit 10. In this example, internal catheters 12 positioned in-vivo/interior to the body fluidly couple together via the subarachnoid space. To that end, a first internal catheter 12 fluidly couples a prescribed region of the brain (e.g., the ventricle) to a first port 16, which itself is configured and positioned to be accessible by external components. In a corresponding manner, a second catheter couples the lumbar region or the lower abdomen of the subarachnoid space with a second port 16 that, like the first port 16, also is configured to be positioned and accessible by external components. The first and second ports 16 may be those conventionally used for such purposes, such as a valved Luer-lock or removable needle. The first and second internal catheters 12 thus may be considered to form a fluid channel extending from the first port 16, to the ventricle, down the spine/subarachnoid space to the lumbar, and then to the second port 16. These internal components, which may be referred to as "internal CSF circuit components," are typically surgically implanted by skilled professionals in a hospital setting.

The CSF circuit 10 also has external components (referred to as "external CSF circuit components). To that end, the external CSF circuit components include at least two fluid conduits 14. Specifically, the external CSF circuit components include a first external fluid conduit 14, that couples with the first port 16 for access to the ventricle. The other end of the first external conduit 14 is coupled with a management system 19, which includes one or more CSF pumps (all pumps are generically identified in the figures as reference number "18"), one or more user interface/displays 20, one or more drug pumps 18, and a control system/controller 22. The fluid external fluid conduit 14 may be implemented as a catheter and thus, that term may be used interchangeably with the term "conduit" and be identified by the same reference number 14.

Illustratively, this management system 19 is supported by a conventional support structure (e.g., a hospital pole 24 in FIG. 1A). To close the CSF circuit 10, a second external catheter 14 extends from that same CSF management system 19 and couples with the second port 16 and the management system 19. This management system 19 and external catheters 14 therefore form the exterior part of a closed CSF circuit 10 for circulating the CSF and therapeutic material.

It should be noted that the CSF circuit 10 may have one or more components between the first and second ports 16 and the respective removable connections of the first and second external catheters 14. For example, the first port 16 may have an adapter that couples with the first external catheter 14, or another catheter with a flow sensor may couple between such external catheter 14 and port 16. As such, this still may be considered a removable connection, albeit an indirect fluid connection. There may be corresponding arrangements with the other end of the first external catheter 14, as well as corresponding ends of the second external catheter 14. Accordingly, the connection can be a direct connection or an indirect connection.

The first and second external catheters 12 and 14 preferably are configured to have removable connections/couplings with the management system 19, as well as their respective ports 16. Examples of removable couplings may include a screw-on fit, an interference fit, a snap-fit, or other known removable couplings known in the art. Accordingly, a removable coupling or removable connection does not necessarily require that one forcibly break, cut, or otherwise permanently break the ports 16 for such a connection or disconnection. Some embodiments, however, may enable a disconnection form the first and/or second ports 16 via breaking or otherwise, but the first and/or second ports 16 should remain in-tact to receive another external catheter 14 (e.g., at the end of life of the removed external catheter 14).

FIG. 1B schematically shows more details of the first and/or second external conduits/catheters 14. This figure shows an example of an external catheter 14 operating with other parts of the system. As shown, the system receives a drug reservoir 17 (e.g., a single-use syringe) configured to deliver a dose of therapeutic material (e.g., a drug) that fluidly couples with the catheter 14 via a check valve 28 and T-port 19 on the catheter 14. In addition, the catheter 14 is coupled with a mechanical pump 18 and also preferably includes a sample port 23 with flow diverters 25 for diverting flow toward or away from a sample port 23. The sample port 23 preferably has sample port flow sensors 23A to track samples.

Some embodiments may be implemented as a simple catheter having a body forming a fluid-flow bore with removably couplable ends (or only one removably couplable end). Illustrative embodiments, however, add intelligence to make one or both of these external catheters 14 "smart" catheters, effectively creating a more intelligent flow system. For example, either one or both of the external catheters 14 can have a processor, ASIC, memory, EEPROM (discussed below), FPGAs, RFID, NFC, or other logic (generally identified as reference number "27") configured to collect, manage, control the device, and store information for the purposes of security, patient monitoring, catheter usage, or communicating with the management system 19 to actively control fluid dynamics of the CSF circuit 10. Among other things, the management system 19 may be configured to coordinate with an EEPROM 27 to control CSF fluid flow as a function of the therapeutic material infusion flow added to the CSF circuit 10 (discussed below) via the check valve 28 at the output of the drug reservoir 17.

As shown in FIG. 1B, one embodiment of the external catheter 14 has the noted electrically erasable programmable read-only memory, EEPROM 27, (or other logic/electronics) that can be implemented to accomplish a variety of functions. Among others, the EEPROM 27 can ensure that the CSF circuit 10 and its operation is customized/individualized to a patient, a treatment type, a specific disease, and/or a therapeutic material. For example, in response to reading information stored in the EEPROM 27, the control system 22 may be configured to control fluid flow as a function of the therapeutic material.

Importantly, as a disposable device, the EEPROM 27 or other logic of the external catheter 14 can be configured to provide alerts, and/or produce or cause production of some indicia (e.g., a message, visual indication, audio indication, etc.) indicating that the external catheter 14 has reached an end of its lifecycle, or indicating how much of its lifecycle remains. For example, an external surface of the catheter 14 may have a tag that turns red when the EEPROM 27 and/or other logic 27 determines that the external catheter 14 has reached its full lifetime use. For example, the external catheter 14 may be considered to have a usage meter, implemented as some logic or EEPROM 27, configured to track use of the CSF fluid conduit 14 to help ensure it is not used beyond its rated lifetime. Moreover, the logic or EEPROM 27 can register with the control system 22 to start use timers to reduce tampering or use beyond a lifetime.

Some embodiments have a printable circuit board (PCB) equipped with a wireless interface (e.g., Bluetooth antenna) or a hardware connection configured to communicate the pump 18 and/or control system 22. The external catheter 14 can be configured to time out after a certain period, capture data, and communicate back and forth with the control system 22 or other off-catheter or on-catheter apparatus to share system specifications and parameters. The intelligent flow catheter 14 can be designed with proprietary connections such that design of knockoffs or cartridges 26 (discussed below) can be prevented to ensure safety and efficacy of the CSF circuit 10 and accompanying processes.

In addition to the management logic, the external catheter(s) 14 also may have a set of one or more flow sensors and/or a set of one or more pressure sensors. Both of those flow sensors are shown generically at reference number 29, and may be located upstream or downstream from their locations in FIG. 1B. For example, the left sensor(s) 29 generically shown in FIG. 1B can be a flow sensor, pressure, or both a flow sensor and pressure. The same can be said for the right sensor(s) 29 generically shown in FIG. 1B. They preferably are positioned between the ports 16 on the body and the remaining components as shown.

Of course, the flow sensor(s) 29 may be configured to detect flow through the bore of the catheter body, while the pressure sensor(s) 29 may be configured to detect pressure within the bore of the body. Among other functions, the flow sensor(s) 29 may monitor flow rate of fluid through the conduit bore and/or total flow volume through the conduit bore.

The catheter 14 preferably is configured to have different hardness values at different locations. Specifically, illustrative embodiments may use a mechanical pump 18, as shown and noted above. The pump 18 may periodically urge a compressive force along that portion of the catheter 14 it contacts at its interface 18A with the catheter 14. The outlet of the pump 18 in this case may be the portion of the catheter 14 that is receiving the output of a neighboring compressed catheter portion (e.g., a portion that is adjacent to the compressed catheter portion(s). To operate efficiently, illustrative embodiments form the catheter 14 to have a specially configured hardness at that location (e.g., 25-35 Shore A). Diameter also is important for flow and thus, one skilled in the art should determine appropriate diameters as a function of performance and durometer/hardness. Preferably, the catheter portion that contacts the pump 18 is softer than the remainder of the catheter 14, although both could have the same hardness. Accordingly, the catheter preferably has a variable hardness along its length and may even have a variable diameter.

Alternative embodiments may provide an open-loop CSF fluid circuit 10. For example, the CSF fluid circuit 10 may have an open bath (not shown) to which fluid is added and then removed. The inventors expect the closed-loop embodiment to deliver better results, however, than those of the open-loop CSF fluid circuit 10.

Illustrative embodiments are distributed to healthcare facilities and/or hospitals as one or more kits. For example, one more inclusive kit may include the internal and external catheters 12 and 14. Another exemplary kit may include just the internal catheters 12 and the ports 16 (e.g., for a hospital), while a second kit may have the external catheters 14 and/or a single-use syringe. Other exemplary kits may include the external catheters 14 and other components, such as the management system 19 and/or a CSF treatment cartridge 26. See below for various embodiments of the CSF circuit 10 and exterior components that also may be part of this kit.

In some embodiments, the kit may include a number of other or similar items. For example, the kit may include an antisense oligonucleotide material (ASO) and a fluid management circuit with a pump, catheter, access port, and mechanical couplings. Some of those features, such as the access port, may be integrated into the other components. For example, the access port may be part of the catheter, or a separate component. As another example, the mechanical couplings may be integral with the catheter or separate.

Accordingly, when coupled, these pumps 18, valves (discussed below and all valves generally identified by reference number 28), internal and external catheters 14, and other components may be considered to form a fluid conduit/channel that directs CSF to the desired locations in the body. It should be noted that although specific locations and CSF containing compartments are discussed, those skilled in the art should recognize that other compartments can be managed (e.g., the lateral ventricles, the lumbar thecal sac, the third ventricle, the fourth ventricle, and/or the cisterna magna). Rather than accessing the ventricle and the lumbar thecal sac, both lateral ventricles could be accessed with the kit. With both internal catheters 12 implanted, CSF may be circulated between the two lateral ventricles, or a drug could be delivered to both ventricles simultaneously.

In illustrative embodiments, the CSF management system 19 generally manages fluid flow to target anatomy through the CSF circuit 10. To that end, that management system 19 has at least one pump 18 that directs flow of the CSF, and at least one pump 18 that directs flow of a therapeutic material (e.g., a drug) though the CSF circuit 10 to desired anatomy. Alternative embodiments may have more pumps 18 for these functions, or combine pumps 18 for these functions. The management system 19 also has a plurality of valves 28 to control flow, and the control system 22, as noted, is configured to control the pumps 18 to selectively apply the drug-carrying CSF to desired local anatomy. Figure lA also shows a user interface 20 that enables a clinician to control drug and fluid parameters in the CSF circuit 10 (discussed below) via the control system 22.

Some embodiments may use a monitoring process, such as real-time spectroscopy, to monitor drug concentrations in the CSF. In some of these embodiments, a spectrophotometric sensor may be placed in the CSF circuit 10 to measure the localized concentration of a substance based on its absorption at various wavelengths. For example, some embodiments may use a sensor constructed to measure a single wavelength or multiple wavelengths. The reading taken by the sensor may be relayed to the control system 22, where it would then be stored or processed for various purposes. This signal could be processed for a number of purposes, such as to trigger the control system 22 to alter the fluid flow, flow direction, and/or frequencies of certain periodic flows of bodily fluids (e.g., CSF) to provide a more localized and efficient therapeutic application to a patient in real-time. It will be appreciated that the signal could also be stored or displayed such that the changes to flow, direction or frequencies of period flows could be adjust manually.

FIG. 1C shows a high level surgical flow process that may incorporate the CSF circuit 10 of FIG. 1A in accordance with illustrative embodiments of the invention. It should be noted that this process is substantially simplified from a longer process that normally would be used to complete the surgical flow. Accordingly, this process may have many additional steps that those skilled in the art likely would use. In addition, some of the steps may be performed in a different order than that shown, or at the same time. Those skilled in the art therefore can modify the process as appropriate. Moreover, as noted above and below, many of the materials, devices, and structures noted are but one of a wide variety of different materials and structures that may be used. Those skilled in the art can select the appropriate materials and structures depending upon the application and other constraints. Accordingly, discussion of specific materials, devices, and structures is not intended to limit all embodiments.

The process begins at step 100 by setting up the internal catheters 12 inside the patient. To that end, step 100 accesses the ventricles and thecal sacs using standard catheters and techniques, thus providing access to the CSF. Step 102 then connects access catheters 12 to peritoneal catheters 12, which are tunneled subcutaneously to the lower abdomen. The tunneled catheters 12 then are connected at step 104 to the ports 16 implanted in the abdomen.

At this point, the process sets up an extracorporeal circulation set (i.e., the external catheters 14, or the "smart catheters" in some embodiments). To that end, step 106 may prime and connect the extracorporeal circulation set 14 to the subcutaneous access ports 16. Preferably, this step uses an extracorporeal circulation set, such as one provided by Enclear Therapies, Inc. of Newburyport, Mass., and/or the external catheters 14 discussed above. The process continues to step 110, which connects an infusion line or other external catheter 14 to the management system 19, and then sets the target flow rate and time. At this point, setup is complete and treatment may begin (step 112).

The process then removes endogenous CSF from the ventricle. This CSF may then be passed through a digestion region (e.g., through a cartridge 26 having a specific digesting material), where certain target proteins in the CSF are digested. For example, the cartridge 26 may have an inner plenum space 1830 of the cartridge 26 filled with a plurality of (e.g., porous, chromatography resin) beads that have been compression packed. To prevent constituents from entering or escaping from the cartridge 26, a filter membrane may be disposed at the first end of the cartridge 26 and a second filter membrane may be disposed at the second end of the cartridge 26. In some applications, the ameliorating agent may be decorated on the beads 1835.

In some applications, the cartridge 26 may be compression packed with a chromatography resin (e.g., agarose, epoxy methacrylate, amino resin, and the like) that has a protease covalently bonded (i.e. immobilized) to the three-dimensional resin matrix. The selected protease may be configured to degrade and/or removing target toxic biomolecules by way of proteolytic degradation. The resin may be a porous structure having a particle size commonly ranging between 75-300 micrometers and, depending on the specific grade, a pore size commonly ranging between 300-1800 Å. Thus, at a high level, the cartridge 26 has ameliorating agent that removes and/or substantially mitigates the presence of toxic proteins from the CSF.

This and similar embodiments may consider this to be an input for the digesting enzyme. Any location providing access to the drug may be considered to be an input for the drug. At step 116, the treated CSF exits the digestion region and is returned via the CSF circuit 10 to the lumbar thecal sac. The process concludes at step 118, which stops the pump 18 when treatment is complete. The management system 19 then may be disconnected and the ports 16 flushed.

In accordance with illustrative embodiments, the CSF circuit 10 is configured to improve the likelihood of the drug passing through the blood-brain barrier. To that end, the management system 19 enables the user or logic to independently set both the flow rate of CSF circulation (e.g., between 0.05 ml/min and 2.0 ml/min, such as 0.5 ml/min) and the dosing rate of the drug (e.g., between 0.01 ml/min to 2.0 ml/min, such as 0.02 ml/min). Preferably, these rates are different, although they can be the same. In illustrative embodiments, the CSF circulation rate is controlled to be different from the natural CSF flow rate. Note that the natural CSF flow rate is the rate of CSF flow without intervention by outside equipment, such as the pumps 18 and other CSF circuit components—even if it is within a range of typical non-interventionally controlled CSF flow rates. Thus, unless the context dictates otherwise, the non-natural CSF flow rate is the flow rate with such intervention. In other embodiments, the CSF flow rate is simply changed from its truly natural flow rate—i.e., the rate at which the CSF flows without intervention.

Depending on a number of factors, the CSF flow rate may be greater than the rate of drug infusion, while in other embodiments, the CSF flow rate is less than rate of the drug infusion rate. Other embodiments may set them to be equal. Those skilled in the art can select the appropriate flow rate based on a variety of factors, including the drug being delivered, the illness, patient profile, rated pressure of the CSF circuit 10, etc.

The inventors recognized that varying the two rates in a coordinated manner enables more control of the drug dose as well as more control of the drug treatment time. Stated another way, these two independent flow rates enable setting of the dosing rate, which allows the user to optimize drug concentration. At the same time, having the ability to set the flow rate allows the user to control the rate of delivery (as opposed to relying upon natural CSF flow).

As noted in the example below, the inventors were surprised to discover that varying the rates in this manner enabled penetration of the drug across the otherwise difficult to penetrate blood-brain barrier. The selected CSF flow rate may be constant or variable. For example, the CSF flow rate may be set to a first rate for a first period of time, a second rate for a second period of time, and a third rate for a third period of time. As such, various embodiments enable flow of the CSF within the CSF circuit 10 at two or more flow rates at two or more different times. The drug delivery rate may be constant or variable in a similar manner, but coordinated with the CSF flow rate to deliver preferred results.

The inventors recognized that a wide variety of different CSF circuit configurations can accomplish the desired goals. FIG. 2 schematically shows a two pump CSF circuit 10 with the drug fed into the pump 18 through a separate fluid line/catheter 12/14 in accordance with illustrative embodiments. In a corresponding manner, FIG. 3 schematically shows a two pump CSF circuit 10 with drug introduced directly into fluid line.

In one embodiment, the CSF circuit 10 has two pumps 18, Pump 1 and Pump 2, to enable a user to set flow rate and dosing rate independently. To that end, Pump 1 may be programmed to control the rate of CSF circulation, while Pump 2 may be programmed to control the dosing rate of the drug to be delivered. Both pumps 18 could be programmed to achieve a desired delivery profile. Check valves 28 or other flow control devices prevent backflow into either pump 18.

As show, the drug may be fed into the pump 18 through a separate fluid line/catheter (FIG. 2) and input to mix with the patient's CSF in the internal catheter/tubing set 12 before being reintroduced to the body. Alternatively, the drug may also be pre-loaded into a cartridge 26 or other type of drug reservoir and connected directly into the fluid line/catheter 14 (FIG. 3). In this latter embodiment, the CSF mixes with the drug as it flows through the cartridge 26 and tubing set 12/14. FIG. 4A schematically shows another embodiment in which a flow control valve 28 is used in place of Pump 2. In this embodiment, that flow control valve 28 preferably is programmed to control the dosing rate (i.e., the rate of adding the drug to the CSF circuit 10 carrying the CSF.

FIG. 5 schematically shows a two-pump circuit 10 with a mixing chamber 30 in accordance with illustrative embodiments. In particular, to ensure a homogeneous mixture of CSF and the drug being delivered, the noted mixing chamber 30 is added to both the two-pump circuit 10 (FIG. 5) and the flow control valve 28 circuit (FIG. 6). The mixing chamber 30 can contain a sensor that provides a readout of a drug's concentration in the CSF, or the management system 19 could simply be programmed to produce a specific drug concentration in the CSF.

In FIG. 5, the CSF-circulating pump 18 and the dosing pump 18 (via an input) feed into the mixing chamber 30 at independent programmable rates. Upon entering the chamber, a small turbine mixes the fluids and the homogeneous mixture is expelled and returned to the patient anatomy. The same concept applies to FIG. 6, but some in-line mixing occurs before the fluids reach the mixing chamber 30.

Whether controlling dosing rate by a second pump 18 or by a flow control valve 28, CSF delivery may be manually programmed on an interface/display 20 similar to FIGS. 7 and 8. Specifically, FIGS. 7 and 8 schematically show two different user interfaces 20 in accordance with illustrative embodiments. Rather than requiring the user to input a dosing rate, however, the user may specify a drug concentration and the management system 19 responsively may adjust the dosing rate accordingly to achieve that concentration. The user can also input a maximum dosage. After this dosage was reached, the management system 19 would automatically stop treatment. FIG. 8 shows one such interface 20 (e.g., a graphical user interface or a manual interface).

It should be noted that the during actual processing, the CSF flow rate may differ at different parts of the CSF circuit 10—total CSF flow rate in the CSF circuit 10 is not necessarily homogenous. For example, some parts of the CSF circuit 10 may be wider (e.g., certain human geographies) and thus, may be slower than the average CSF circuit flow rate, while other portions may be narrower, causing a nozzle effect and increasing the CSF flow rate at that point. Near the pump 18 (e.g., at the pump outlet), however, the CSF flow rate can be controlled to provide a desired rate across the entire CSF circuit 10, even if that rate may deviate in local parts of the CSF circuit.

The discussion above relates to delivering a therapeutic material, such as a drug, over a longer infusion period (e.g., 5 minutes, 10 minutes, 30 minutes, 1-6 hours, days, etc.). FIG. 9 shows another embodiment that localizes drug delivery at a target area of the brain using a bolus drug infusion. Specifically as known by those in the art, a dose of drug can be delivered in a short time period (e.g., 10 seconds, 20 seconds, 60 seconds), or over a longer period (i.e., gradual drug administration, as noted above). The shorter drug delivery is known in the art as a "bolus" drug delivery.

Specifically, to optimize delivery, FIG. 9 alternates the flow direction of the pump 18. The pump 18 thus has programmable controls, via the control system 22, for flow rate and frequency of these alternations. The flow rate and frequency preferably are programmed to achieve a desired delivery profile.

In a manner similar to the other process discussed above, the process of FIG. 9 is substantially simplified from a longer process that normally would be used to complete the localize drug delivery. Accordingly, this process may have many additional steps that those skilled in the art likely would use. In addition, some of the steps may be performed in a different order than that shown, or at the same time. Those skilled in the art therefore can modify the process as appropriate. Moreover, as noted above and below, many of the materials, devices, and structures noted are but one of a wide variety of different materials and structures that may be used. Those skilled in the art can select the appropriate materials and structures depending upon the application and other constraints. Accordingly, discussion of specific materials, devices, and structures is not intended to limit all embodiments.

FIG. 9 therefore delivers a drug intrathecally using positive displacement at a desired flow rate. It may incorporate the components discussed above, as well as principles discussed for other embodiments, such as that discussed above with regard to FIG. 2. The process of FIG. 9 begins at step 900 by adding the drug in a bolus dose to the CSF circuit 10, and/or administering a tag for imaging to the drug. In the latter example, its position can then be tracked using standard imaging techniques to determine when the drug has reached the target anatomy. Alternative embodiments add the drug to the CSF without administering a tag. Such steps may use other techniques to ensure the drug is localized at the desired target anatomy.

Step 902 sets the desired flow rate, direction, timing, and other parameters for the CSF circuit 10 to accomplish the bolus application. For example, specific computer program code on a tangible medium within the control system 22 may cooperate with other components of the CSF circuit 10 to control addition of the therapeutic material, localize the therapeutic material, or both. Next, after step 904 verifies the position of the drug at a target anatomy, step 906 controls the pump 18 to maintain the drug at that target location. Among other ways, step 906 may control the pump(s) 18 to oscillate at a desired flow rate and frequency to contain the drug at that prescribed or desired anatomical location for a pre-set period of time.

After the bolus reaches the target anatomy, the pump 18, which can be programmable and/or have logic, can reverse CSF flow; specifically, the pump 18 can alternate quickly between pushing and pulling flow of the CSF so that the bolus of drug is localized to the target anatomy in the brain (or another target anatomy). In other words, the higher concentration of drug in a portion of the CSF can moved back and forth over the target region. Other embodiments can simply slow down the CSF flow rate to ensure a longer drug application to the target. Either way, these embodiments preferably "soak" the target with the drug, providing a higher quality drug administration. As a result, despite using less of the drug than would be administered by prior art systems, this embodiment still administers a desired amount of the drug to the target by this localizing technique, consequently minimizing toxicity and drug costs (step 908).

It should be noted that "reaching" the target anatomy may be defined by the user or other entity within the control system 22. For example, the portion of CSF in the CSF circuit 10 having the higher concentration of drug (from the bolus) may be considered to have reached the target anatomy when some identifiable portion of it (e.g., the highest concentration, or an interior point within the spread of the drug in the CSF) may be within a prescribed distance upstream of the target, or a prescribed distance downstream of the target. Some embodiments may require the defined portion of CSF with the high drug concentration to actually be at or in contact with that target region. Other embodiments may consider the drug to have "reached" the target simply by calculating the time it should take to reach that area, using artificial intelligence/machine learning, and/or through empirical studies.

Illustrative embodiments can be implemented in a number of different manners with catheters 12/14, pumps 18, valves 28, etc. similar to those discussed above (including the noted external catheters 14). FIGS. 10-14 show several exemplary implementations. In the embodiment shown in FIG. 10, the CSF circuit 10 has four pinch valves 28 on tubing (i.e., external catheters 14), enabling fluid oscillation between opposing flow directions. To flow from lumbar to ventricle (FIG. 10), pinch valves 1 and 2 are opened while pinch valves 3 and 4 are closed. Conversely, to switch flow direction from ventricle to lumbar (FIG. 11), pinch valves 1 and 2 are closed while pinch valves 3 and 4 are opened. Controlling the pinch valves 28 in this manner enables flow direction oscillation. The frequency at which the pinch valves 28 switched between open and closed may be set by the user as could the flow rate of the pump 18 (e.g., via the control system 22). Alternative embodiments may pre-program such parameters into the management system 19.

In fact, the same pinch valve 28 configuration (FIG. 12) may be used to create a pulsatile flow pattern. For example, when flowing from lumbar to ventricle, pinch valves 3 and 4 remain closed, while pinch valves 1 and 2 are pulsed (i.e., periodically switched between open and closed) at a frequency set by the user. The ability to set the frequency at which the pinch valves 28 open and close enables a range of pulsatile effects to be implemented. For example, rather than rapidly switching between open and closed pinch valves 28, the valves 28 can remain closed long enough to build up a set pressure in the fluid line. Shortly after opening the pinch valves 28, a bolus of the drug can be released as a result of the pressure build-up.

Flow direction oscillation and a pulsatile flow pattern could also be produced using a bidirectional pump 18 instead of using pinch valves 28 (e.g., FIG. 13A and FIG. 13B). The pump 18 can be programmed to switch flow directions at a frequency set by the user. While flowing in one direction, the pump 18 can be programmed to pulse by starting and stopping at a frequency also set by the user. Those skilled in the art may use other techniques to provide bidirectional flow.

In addition to those noted above, some embodiments may set the frequency, flow rate, and other parameters as a function of the requirements and structure of the anatomy and devices used in the treatment (e.g., in the CSF circuit 10). Among others, those requirements may include the diameter of the catheters in the CSF circuit 10, physical properties of the drug, the interaction of the drug at the localized region, the properties of the localized region, and other requirements and parameters relevant to the treatment. Those skilled in the art may select appropriate parameters as a function of the requisite properties.

FIG. 14 schematically shows another system interface 20 configured in accordance with illustrative embodiments. Specifically, whether controlling delivery parameters by pinch valve, a bidirectional pump 18, or other means, the delivery profile can be controlled manually with an interface 20, such as the interface 20 shown in FIG. 14, and/or a delivery profile loaded onto the management system 19. As with the other interfaces, this interface 20 may be a fixed control panel, or a graphical user interface on a display device.

FIG. 15 shows a process of manually programming drug delivery of a bolus in accordance with illustrative embodiments. In a manner similar to the other process discussed above, this process is substantially simplified from a longer process that normally would be used to complete the localize drug delivery. Accordingly, this process may have many additional steps that those skilled in the art likely would use. In addition, some of the steps may be performed in a different order than that shown, or at the same time. Those skilled in the art therefore can modify the process as appropriate. Moreover, as noted above and below, many of the materials, devices, and structures noted are but one of a wide variety of different materials and structures that may be used. Those skilled in the art can select the appropriate materials and structures depending upon the application and other constraints. Accordingly, discussion of specific materials, devices, and structures is not intended to limit all embodiments.

The process begins at step 1500, which sets the flow direction. Three options include lumbar to ventricle (1502A), ventricle to lumbar (step 1502B), or oscillating between flow directions (step 1502C). Next, the process sets the flow rate at steps 1504A or 1504B, and sets the frequency of the pulse (step 1506A) or oscillation frequency (step 1506B). Alternative embodiments can be programmed using artificial intelligence algorithms or other program logic.

EXAMPLE 1: ADMINISTRATION OF METHOTREXATE TO A SHEEP USING ILLUSTRATIVE EMBODIMENTS

Figure 16A:
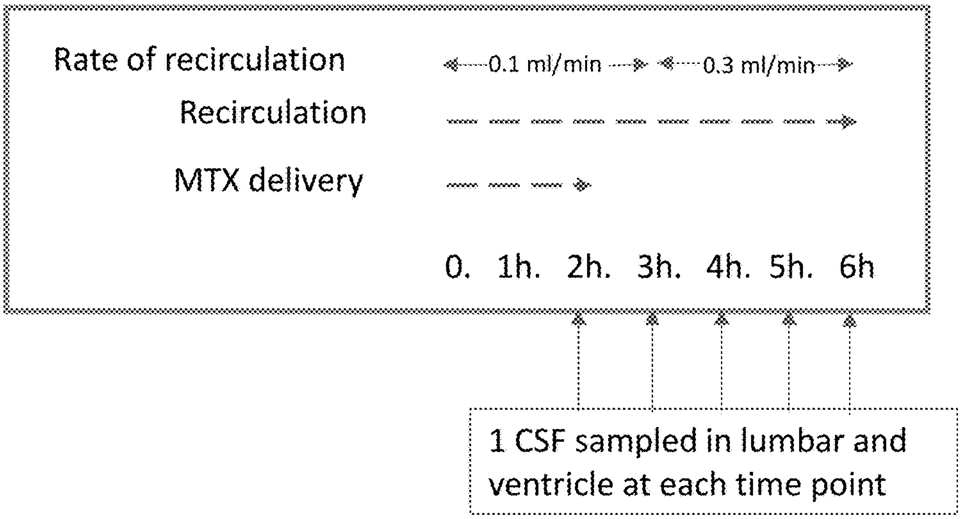
FIGS. 16A, 16B, and 16C detail an example of illustrative embodiments of the invention.
Figure 16B:
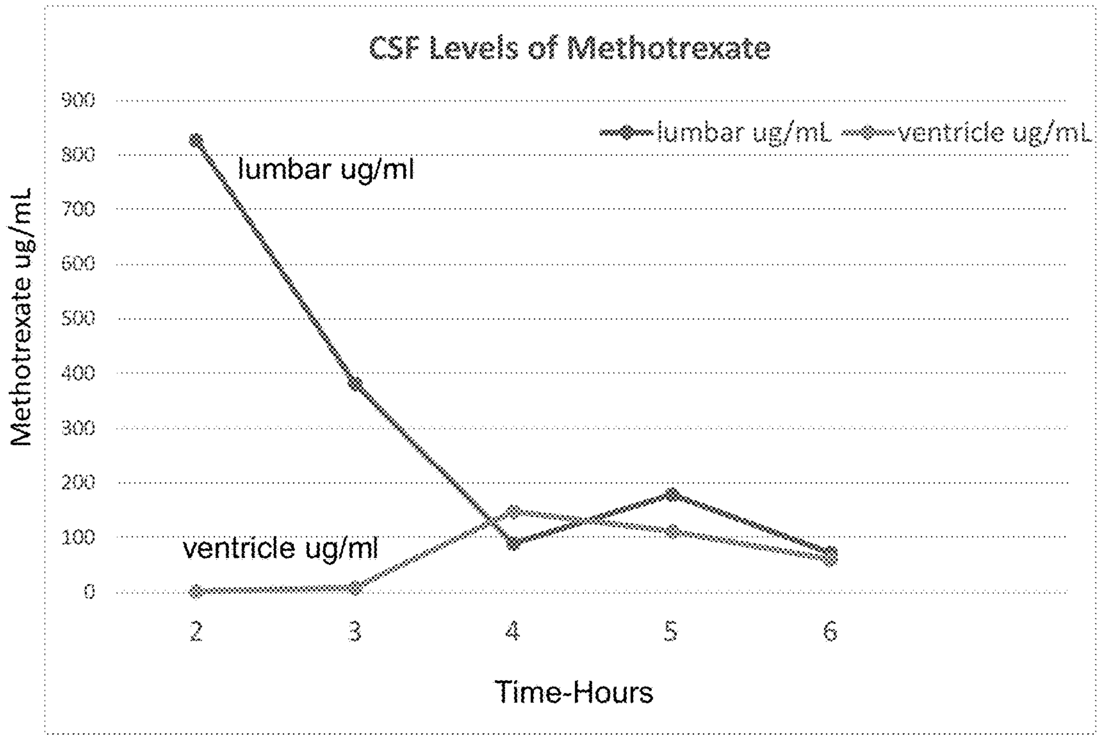
Figure 16C:
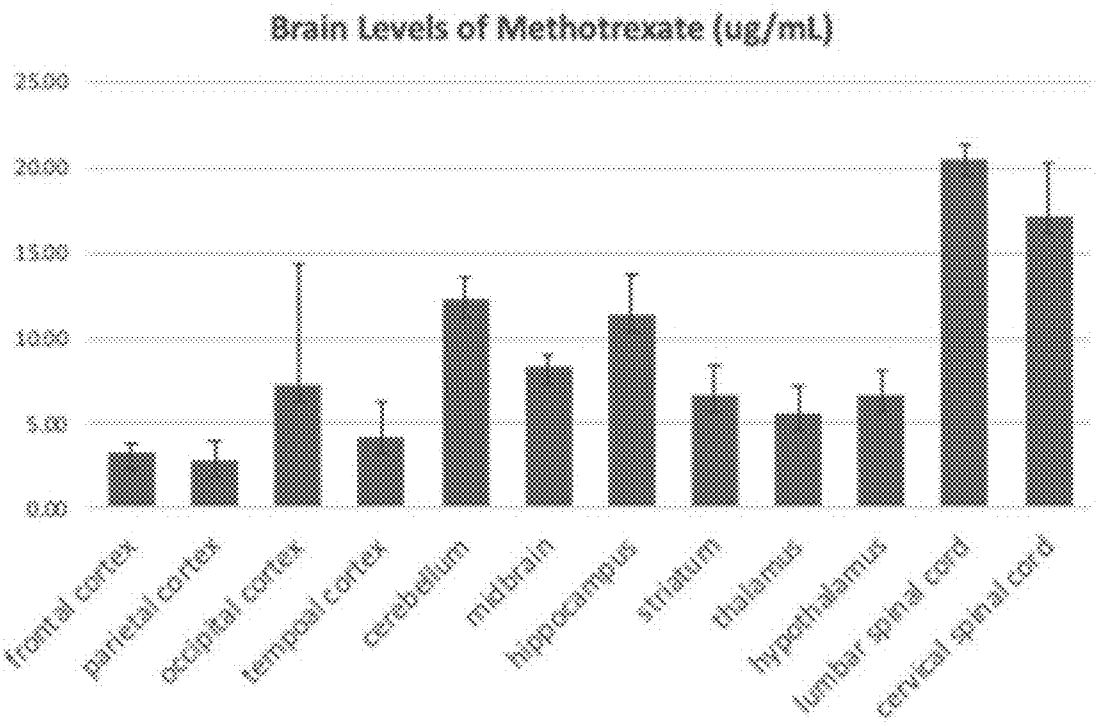

The inventors administered methotrexate to sheep using illustrative embodiments. An outline of the study is depicted by FIGS. 16A-16C. A sheep used for this experiment received the CSF circuit 10 of illustrative embodiments. Circulation was started at the same time that methotrexate was infused. Methotrexate was infused at a gradual rate of 2 mLs over 2 minutes and then recirculation from lumbar to ventricle was started at a rate of 0.2 mLs/min. Circulation continued after drug infusion was stopped for four more hours. At zero to three hours, the circulation rate was at 0.1 mL/min and from four to six hours, circulation was at 0.3 mL/min. The dose of methotrexate infused was 12 mg. Drug concentration was measured with LC/MS (liquid chromatography with the mass analysis capabilities of mass spectrometry) in the CSF, spinal cord, and multiple brain regions.

FIG. 16B schematically shows the results. CSF levels of methotrexate were analyzed over time. Drug levels were found to be very high in the lumbar region where the drug was infused and a decline over time was measured except for an increase at 5 hours and then a subsequent decline. CSF levels of methotrexate were very low in the ventricular samples initially, but with time, increased at 4 and 5 hours, before declining to a similar level as the lumbar samples.

FIG. 16C shows how samples from twelve regions of the brain were homogenized and analyzed for methotrexate levels and measured as ug/mL/g of tissue. The x-axis of this graph is drug levels. All areas of the brain and spinal cord had good levels of methotrexate. It will be appreciated that methotrexate that is administered typically subdural in the thigh typically does not cross the blood-brain barrier and would not be found in appreciable levels in brain and spinal cord as a result.

EXAMPLE 2: ADMINISTRATION OF ANTISENSE OLIGONUCLEOTIDE TO A SHEEP USING ILLUSTRATIVE EMBODIMENTS

The inventors administered an antisense oligonucleotide (ASO) for Huntington's disease to sheep using illustrative embodiments. An outline of the study is depicted in FIGS. 17A-C. Each sheep used for this experiment received the CSF circuit 10 of illustrative embodiments. Circulation was started at the same time that ASO was infused. ASO was infused at a rate of 2 mLs over 2 min. The dose of ASO infused was 30 mg. Circulation continued after drug infusion was stopped for four more hours. At zero to four hours, the circulation rate was at 0.2 mL/min. For unidirectional flow, the direction of the flow was lumbar to ventricle me for the entire 4 h. For the bidirectional flow, the first 1 h of flow was lumbar to ventricle, then the direction of flow was reversed to ventricle to lumbar for 10 min, then switched repeatedly for 10 min intervals for the remainder of the 4 h. All sheep in the study were necropsied after 48 h and tissues were collected to assay drug levels.

The assay for detection of the ASO is depicted in FIG. 17B. Sandwich hybridization ELISA (Enzyme-Linked-immuno-absorption-Assay) quantification used to measure the concentration of CAG repeats in tissue, CSF, and blood samples. Probes comprised of a sequence complementary to the analyte. Capture DNA probe conjugated to biotin label and applied to a streptavidin-coated microtiter plate. Detection DNA probe with digoxigenin label was used. To detect digoxigenin label, anti-digoxigenin (anti-Dig) peroxidase (POD) is reacted with substrate TMB for the signal measurement by an absorption change with a plate reader.

FIG. 17C schematically shows the results. Samples from seventeen regions of the brain were homogenized and analyzed for ASO levels and measured as ug/g of tissue. The x-axis of this graph is drug levels. Most areas of the brain and spinal cord had good levels of ASO. It will be appreciated that the ASO if administered orally, subdurally, or intravenously typically does not cross the blood-brain barrier and would not be found in appreciable levels in brain and spinal cord as a result.

FIG. 18 shows a method of regulating gene expression of a patient in accordance with illustrative embodiments. It should be noted that this process is substantially simplified from a longer process that normally would be used to regulate gene expression. Accordingly, the process may have additional steps that those skilled in the art likely would use. In addition, some of the steps may be performed in a different order than that shown, or at the same time. Those skilled in the art therefore can modify the process as appropriate. Moreover, as noted above and below, many of the materials and structures noted are but one of a wide variety of different materials and structures that may be used. Those skilled in the art can select the appropriate materials and structures depending upon the application and other constraints. Accordingly, discussion of specific materials and structures is not intended to limit all embodiments.

The method begins with step 1810, which couples a fluid channel between the lumbar region of the patient and the ventricle of the patient's brain. To that end, a physician or other caregiver first may locate an in-vivo lumbar catheter extending from the patient's lumbar, and an in-vivo ventricle catheter extending from the patient's ventricle. After locating those catheters, the ventricle catheter may be mechanically coupled to the lumbar catheter via an intermediate catheter, such as those discussed above, to produce the fluid channel Accordingly, this fluid channel fluidly couples the lumbar and ventricle of the patient. In preferred embodiments, the catheter has a lumen configured to transport ASO mixed with CSF of the patient, and an access port to receive an ASO or other therapeutic.

Step 1820 energizes a pump 18 to cause CSF to flow between the lumbar and the ventricle of the patient.

Next, the physician or other caregiver (e.g., a nurse) adds antisense oligonucleotide material (ASO) to the access port. Indeed, as noted above, this step can be performed before, during, and/or after step 1802—energizing the pump 18. Among other ways, the ASO may be added via a bolus to the fluid channel through the access port. In other embodiments, the ASO may be added more gradually without a bolus as discussed above. Preferably, the fluid channel forms a closed loop configured to circulate CSF and ASO mixture through the ventricle, the body chambers through which CSF flows, the lumbar, and fluid channel in one or two directions. As such, a controller 20/22 or other apparatus may manage the pump 18 to cause the ASO/CF mixture to flow at prescribed, non-natural rates in one direction or in two different directions. As suggested above, some embodiments may oscillate the mixture so that a prescribed region of the brain receives a more concentrated/focused dose of the ASO.

Of course, those skilled in the art should recognize that the above examples are two of many examples that may be used with illustrative embodiments.

Accordingly, illustrative embodiments enable a clinician to more effectively treat various diseases by targeting drug delivery via CSF in the subarachnoid space.

Various embodiments of the invention may be implemented at least in part in any conventional computer programming language. For example, some embodiments may be implemented in a procedural programming language (e.g., "C"), or in an object oriented programming language (e.g., "C++"). Other embodiments of the invention may be implemented as a pre-configured, stand-along hardware element and/or as preprogrammed hardware elements (e.g., application specific integrated circuits, FPGAs, and digital signal processors), or other related components.

In an alternative embodiment, the disclosed apparatus and methods (e.g., see the various flow charts described above) may be implemented as a computer program product for use with a computer system. Such implementation may include a series of computer instructions fixed either on a tangible, non-transitory medium, such as a computer readable medium (e.g., a diskette, CD-ROM, ROM, or fixed disk). The series of computer instructions can embody all or part of the functionality previously described herein with respect to the system.

Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies.

Among other ways, such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). In fact, some embodiments may be implemented in a software-as-a-service model ("SAAS") or cloud computing model. Of course, some embodiments of the invention may be implemented as a combination of both software (e.g., a computer program product) and hardware. Still other embodiments of the invention are implemented as entirely hardware, or entirely software.

The embodiments of the invention described above are intended to be merely exemplary; numerous variations and modifications will be apparent to those skilled in the art. Such variations and modifications are intended to be within the scope of the present invention as defined by any of the appended claims.

What is claimed is:

1. A method of regulating gene expression of a patient, the method comprising:

coupling a fluid channel between the lumbar region of the patient and the ventricle of the patient's brain, the fluid channel fluidly connecting the lumbar region and the ventricle, the fluid channel having an access port and a pump;

energizing the pump to cause CSF to flow at a CSF flow rate between the lumbar and ventricle of the patient; and adding a therapeutic material at a therapeutic material dose rate to the access port before, during, and/or after energizing the pump, wherein, energizing the pump is controlled via a controller;

the controller is configured to control the CSF flow to:
flow from lumbar to ventricle;
flow from ventricle to lumbar; or
oscillate between flow directions, wherein:
the controller is configured to control oscillation of the CSF flow at a frequency selected to offset natural CSF flow based on measured or estimated CSF flow characteristics and thereby retain the therapeutic material within a desired location; and
the CSF flow rate and the dose rate are independently controlled.

2. The method as defined by claim 1 further comprising de-energizing the pump to cause the CSF to flow under natural flow processes, the CSF flowing in one direction only between energizing and de-energizing the pump.

3. The method as defined by claim 1 further comprising de-energizing the pump to cause the CSF to flow under natural flow processes, the CSF flowing in two or more directions between energizing and de-energizing the pump.

4. The method as defined by claim 1 further comprising reversing the direction of the pump output to cause the therapeutic material to pass by the same point in the ventricle or lumbar regions in two directions.

5. The method as defined by claim 1 wherein the fluid channel comprises a catheter having a lumen configured to transport therapeutic material mixed with CSF of the patient.

6. The method as defined by claim 1 wherein adding the therapeutic material comprises adding a bolus of the therapeutic material to the fluid channel through the access port.

7. The method as defined by claim 1 further comprising controlling, via a controller, the pump output rate as a function of a parameter of the patient.

8. The method as defined by claim 1 wherein the fluid channel forms a closed loop configured to circulate CSF and therapeutic material mixture through the ventricle, the body chambers through which CSF flows, the lumbar, and fluid channel in one or two directions.

9. The method as defined by claim 1 wherein the fluid channel comprises a catheter, further wherein coupling a fluid channel between the lumbar region of the patient and the ventricle comprises:
locating a lumbar catheter in-vivo to the patient and extending from the patient's lumbar;
locating a ventricle catheter in-vivo to the patient and extending from the patient's ventricle;
mechanically coupling the catheter to the lumbar catheter;
mechanically coupling the catheter to the ventricle catheter, and
mechanically coupling the fluid channel to the lumbar and ventricle catheters fluidly coupling the lumbar and ventricle of the patient via the fluid channel.

10. A method of regulating gene expression of a patient, the method comprising:
providing fluid management system comprising a pump, a catheter, and an access port that is either part of the catheter or separate from the catheter;
securing together the pump, catheter and access port to form a CSF fluid channel;
coupling the catheter to an internal lumbar catheter extending from and embedded within the patient's the lumbar region;
coupling another end of the catheter to an internal ventricle catheter extending from and embedded within the patient's the ventricle region;
energizing the pump to cause CSF to flow at a CSF flow rate in one or two opposite directions between the lumbar region and ventricle region of the patient, or to oscillate between the two opposite directions; and
adding a therapeutic material at a therapeutic material dose rate to the catheter through the access port before, during, and/or after energizing the pump, wherein energizing the pump is controlled via a controller, wherein:
the controller controls the pump to oscillate CSF fluid flow at a frequency selected to offset natural CSF flow based on measured or estimated CSF flow characteristics to maintain the therapeutic material-within CSF at or near a desired location in the CSF circuit; and
the CSF flow rate and the dose rate are independently controlled.

11. The method as defined by claim 10 further comprising de-energizing the pump to cause the CSF to flow under natural flow processes, the CSF flowing in one direction only between energizing and de-energizing the pump.

12. The method as defined by claim 10 further comprising de-energizing the pump to cause the CSF to flow under natural flow processes, the CSF flowing in two or more directions between energizing and de-energizing the pump.

13. The method as defined by claim 10 further comprising reversing the direction of the pump output to cause the therapeutic material to pass by the same point within the ventricle or lumbar region in two directions.

14. The method as defined by claim 10 wherein the catheter forms a closed loop configured to circulate CSF and therapeutic material mixture through the ventricle, the body chambers through which CSF flows, and the lumbar in one or two directions.

15. The method as defined by claim 10 wherein adding the therapeutic material comprises adding a bolus of the therapeutic material to the catheter through the access port.

16. The method as defined by claim 10 wherein adding the therapeutic material comprises adding a gradual flow of the therapeutic material to the catheter through the access port.

* * * * *